(12) United States Patent
Griffin et al.

(10) Patent No.: US 7,704,943 B2
(45) Date of Patent: Apr. 27, 2010

(54) TRANSGLUTAMINASE FOR INHIBITING ANGIOGENESIS

(75) Inventors: Martin Griffin, Nottingham (GB); Richard Jones, Sheffield (GB)

(73) Assignee: Aston University, Birmingham (GB)

( * ) Notice: Subject to any disclaimer, the term of this patent is extended or adjusted under 35 U.S.C. 154(b) by 872 days.

(21) Appl. No.: 10/344,084

(22) PCT Filed: Aug. 8, 2001

(86) PCT No.: PCT/GB01/03574

§ 371 (c)(1),
(2), (4) Date: Jun. 11, 2003

(87) PCT Pub. No.: WO02/11747

PCT Pub. Date: Feb. 14, 2002

(65) Prior Publication Data

US 2004/0028674 A1   Feb. 12, 2004

(30) Foreign Application Priority Data

Aug. 8, 2000   (GB)   ............................ 0019302.9

(51) Int. Cl.
*A61K 38/00* (2006.01)
*A61K 38/04* (2006.01)
*C07K 14/00* (2006.01)

(52) U.S. Cl. .......................... 514/2; 530/350
(58) Field of Classification Search ................ 424/94.1; 514/2; 382/115, 118, 120
See application file for complete search history.

(56) References Cited

U.S. PATENT DOCUMENTS 5,885,808 A    3/1999  Spooner et al. .......... 435/172.3
6,852,318 B1 *  2/2005  Varner ..................... 424/130.1

OTHER PUBLICATIONS

Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Gura (Science, 1997, 278:1041-1042).*
Winter et al (TIPS, 1993, 14:139-143).*
Baselga et al (J. Clin. Oncol, 1996, 14:737-744).*
Weiner (Seminars Oncology, vol. 26, No. 4, 1999, pp. 41-50).*
Jain (Sci. Am., 1994, 271:58-65).*
Achyuthan et al., "Identification of a Guanosine Triphosphate-binding Site on Guinea Pig Liver Transgluatminase" J. of Biol. Chem 262(4):1901-1906, 1987.
Achyuthan et al., "Immunochemical Analyses of Human Plasma Fibronectin-cytosolic Transglutaminase Interactions" J. of Immun. Methods 180:69-79, 1995.
Bazzoni et al., "Endothelial Adhesion Molecules in the Development of the Vascular Tree:" Curr. Opin. Cell Biol. 11:573-581, 1999.

Bell et al., "Differential Gene Expression During Capillary Morphogenesis in 3D Collagen Matrices:" J. Cell. Sci 114:2755-2773, 2001.
Brown et al., "Critical Evaluation of ECV304 as a Human Endothelial Cell Model Defined by Genetic . . . " Laboratory Investigation 80(1):37-45, 2000.
Burchell et al., "Development and Characterization of Breast Cancer Reactive Monoclonal Antibodies . . . " Cancer Res. 47:5476-5482, 1987.
Clark et al., "Role of the Bp35 Cell Surface Polypeptide in Human B-cell Activation" Proc. Nat'l. Acad. Sci USA 82:1766-1770, 1985.
Dallabrida et al., "Factor XIIIa Supports Microvasculat Endothelial Cell Adhesion and Inhibits Capillary Tube Formation in Fribrin" Blood 95(8):2586-2592, 2000.
Dubbink et al., "Human Prostate-Specific Transglutaminase: A New Prostatic Marker with a Unique Distribution Pattern" Laboratory Investigation 79(2):141-150, 1999.
Folkman, J., "Angiogenesis in Cancer, Vascular, Rheumatoid and other Disease" Nat. Med. 1:27-31, 1995.
Gaudry et al., "Tissue Transglutaminase Is an Important Player at the Surface of Human Endothelial Cells . . . " Exp. Cell Res. 252:104-113, 1999.
Gentile et al., "Isolation and Characterization of cDNA Clones to Mouse Macrophage and Human Endothelial Cell Tissue Transglutaminases" J. of Biol. Chem. 266(1):478-483, 1991.
Greenberg et al., "The Transglutaminase in Vascular Cells and Tissues Could Provide and Alternative Pathway for . . . " Blood 70(3):702-709, 1987.
Greenberg et al., "Transgluatminases: Multifunctional Cross-Linking Enzymes that Stabilize Tissues" FASEB J. 5:3071-3077, 1991.
Grundmann et al., "Characterization of cDNA Coding for Human Factor XIIIa" Proc. Nat'l. Acad. Sci. USA 83:8024-8028, 1986.
Haroon et al., "Tissue Transglutaminase is Expressed, Active, and Directly Involved in Rat Dermal Wound . . . " FASEB J. 13:1787-1795, 1999.
Haroon et al., "Recombinant Human Tissue Transglutaminase Modifies Angiogenesis and . . . " FASEB J. 10:(abstract)1416, 1996.
Hellstrom et al., "Monoclonal Mouse Antibodies Raised Against Human Lung Carcinoma" Cancer Res. 46:3917-3923, 1986.
Hughes, S., "Functional Characterization of the Spontaneously Transformed Human Umbilical Vein Endothelial . . . " Exp. Cell. Res. 225:171-185, 1996.
Jones et al., "Reduced Expression of Tissue Transglutaminase in a Human Endothelial Cell Line Leads to . . . " J. of Cell. Science 110:2461-2472, 1997.

(Continued)

*Primary Examiner*—Karen A Canella
*Assistant Examiner*—Peter J Reddig
(74) *Attorney, Agent, or Firm*—Morrison & Foerster LLP

(57) ABSTRACT

The present invention relates to use of a transglutaminase in the preparation of a medicament for inhibiting angiogenesis. Preferably, the transglutaminase is a human tissue transglutaminase. Advantageously, the medicament is for treating cancer, rheumatoid arthritis, retinopathy and/or psoriasis. Additionally, the invention relates to compositions comprising a transglutaminase in an amount sufficient to inhibit angiogenesis.

6 Claims, 15 Drawing Sheets

OTHER PUBLICATIONS

Kinsella et al., "Formation of High Molecular Weight Dermatan Sulfate Proteoglycan in Bovine Aortic . . . " J. of Biol. Chem. 265(29):17891-17898, 1990.

Kubota et al., "Role of Laminin and Basement Membrane in the Morphological Differentiation of Human . . . "J. of Cell. Biol. 107:1589-1598, 1988.

Lesort et al., "Distinct Nuclear Localization and Activity of Tissue Transglutaminase" J. of Biol. Chem. 273(20):11991-11994, 1998.

Li et al., "PR39, a Peptide Regulator of Angiogenesis" Nature Medicine 6(1):49-55, 2000.

Martinez et al., "Transglutaminase-Mediated Processing of Fibronectin by Endothelial Cell Monolayers" Biochemistry 33:2538-2545, 1994.

Medina, M., "Glutamine Metabolism: Nutritional and Clinical Significance" J. Nutrition 131:2539S-2542S, 2001.

Meyer et al., "A Novel Vascular Endothelial Growth Factor Encoded by Orf Virus, . . . " The EMBO J. 18(2):363-374, 1999.

O'Reilly et al., "Angiostatin Induces and Sustains Dormancy of Human Primary Tumors in Mice" Nature Medicine 2(6):689-692, 1996.

O'Reilly et al., "Endostatin: An Endogenous Inhibitor of Angiogenesis and Tumor Growth" Cell 88:277-285, 1997.

Preissner et al., "Molecular Crosstalk Between Adhesion Receptors and Proteolytic Cascades in Vascular Remodeling" Thrombosis and Haemostasis 78(1):88-95, 1997.

Risau, W., "Mechanisms of Angiogenesis" Nature 386:671-674, 1997.

Thacher et al., "Keratinocyte-Specific Transglutaminase of Cultured Human Epidermal Cells: . . . " Cell 40:685-695, 1985.

Verderio et al., "Regulation of Cell Surface Tissue Transglutaminase: Effects on Matrix Storage . . . " J. of Histochem. & Cytochem. 47(11):1417-1432, 1999.

Zisch et al., "Covalently Conjugated VEGF-fibrin Matrices for Endothelialization" J. of Controlled Release 72:101-113, 2001.

Dvorak el al., "Tumors: Wounds That Do Not Heal," *The New England Journal of Medicine*, vol. 315:1650-1659 (1986).

Haroon et al., "Tissue Transglutaminase is Expressed as a Host Response to Tumor Invasion and Inhibits Tumor Growth," *Laboratory Investigation*, vol. 79:1679-1686 (1999).

Hwang et al., "Interaction Site of GTP Binding $G_h$ (Transglutaminase II) with Phospholipase C," *The Journal of Biological Chemistry*, vol. 270:27058-27062 (1995).

Iismaa et al., "The Core Domain of the Tissue Transglutaminase $G_h$ Hydrolyzes GTP and ATP," *Biochemistry*, vol. 36:11655-11664 (1997).

Johnson et al., "Transfection of tissue transglutaminase into a highly malignant hamster fibrosarcoma leads to a reduced incidence of primary tumour growth," *Oncogene*, vol. 9:2935-2942 (1994).

Jones et al., "Matrix changes induced by transglutaminase 2 lead to inhibition of angiogenesis and tumor growth," vol. 13:1442-1453 (2006).

Kim et al., "The Structure of the Transglutaminase 1 Enzyme," *The Journal of Biological Chemistry*, vol. 269:27979-27986 (1994).

Lai et al., "C-terminal Deletion of Human Tissue Transglutaminase Enhances Magnesium-dependent GTP/ATPase Activity," *The Journal of Biological Chemistry*, vol. 271:31191-31195 (1996).

Monsonego et al., "Expression of GTP-dependent and GTP-independent Tissue-type Transglutaminase in Cytokine-treated Rat Brain Astrocytes," *The Journal of Biological Chemistry*, vol. 272:3724-3732 (1997).

\* cited by examiner

Angiogenesis *in vitro*: Live pictures of tTGase antisense and control endothelial cells

TRANSGLUTAMINASE FOR INHIBITING ANGIOGENESIS

CROSS-REFERENCE TO RELATED APPLICATIONS

This application is a National Phase application under 35 U.S.C. 371 of International Application No. PCT/GB2001/03574 filed Aug. 8, 2001 and claims the benefit of Great Britain Application No. 0019302.9 filed Aug. 8, 2000.

The present invention provides methods for inhibiting angiogenesis. In particular, the present invention relates to the use of tissue tranglutaminase (tTG or tTGase) in the treatment of solid tumour grow rheumatoid arthritis and psoriasis.

BACKGROUND OF THE INVENTION

Angiogenesis, the sprouting and development of new blood vessels from pre-existing ones, is a fundamental process that occurs in embryonic development and tissue remodelling (Folkman, J., 1995, *Nat. Med.* 1, 27-31). The development of the neovasculature requires the proliferation and migration of endothelial cells, and their interaction with other cell types including fibroblasts and pericytes to form complex three-dimensional cord-like structure that contain endothelial monolayers surrounding the lumen of the vessel (Risau, W., 1997, *Nature* 386, 671-674). The mechanisms controlling angiogenesis are not completely understood, but it is likely that the progression and development of new blood vessels is regulated at multiple control sites, and involves growth factors (Meyer, M et al, 1999, *EMBO J.* 18, 363-374), proteases (Kubota, Y., et al., 1988, *J. Cell Biol.* 107, 1589-1598), the extracellular matrix (Preissner, K. T., et al., 1997, *Thromb. Haemost.* 78, 88-95), and the expression of cell-surface receptors (Bazzoni, G., et al., 1999, *Curr. Opin. Cell Biol.* 11, 573-581). The identification of factors that regulate and control angiogenesis is of increasing clinical importance since inappropriate or insufficient angiogenesis is central to a number of pathological conditions, including the development of solid tumours, rheumatoid arthritis and psoriasis (Folkman, J., 1995, *Nat. Med.* 1, 27-31).

The search for molecules that modulate angiogenesis is of emerging clinical importance, particularly with respect to solid tumor therapy. Specific inhibition of angiogenesis has the potential to revolutionise cancer therapy, by starving tumours of their blood supply (O'Reilly, M. S., et al., 1997, *Cell* 88, 227-285), and this approach to cancer therapy led to the discovery of the anti-angiogenic peptides endostatin (O'Reilly, M. S., et at., 1997, *Cell* 88, 227-285) and angiostatin (O'Reilly, M. S., et al., 1996, *Nat. Med.* 2, 689). Modulation of angiogenesis also presents the possibility of new treatments for other pathological conditions that rely on vascular remodelling.

Transglutaminases are an important class of protein crosslinking enzymes that catalyze protein aggregation reactions in blood coagulation (Greenberg, C. S., et al., 1991, *FASEB J.* 5, 3071-3077), skin maturation Thacher, S. M. & Rice, R. H., 1985, *Cell* 40, 685-695) and the clotting of seminal secretions (Dubbink, H. J., et al., 1999, *Lab. Invest.* 79, 141-150). The most widespread member of the family is the cellular form of the enzyme, tissue transglutaminase (tTGase), which is expressed in varying amounts in many cell types. Like the well-characterized plasma TGase (blood coagulation factor XIIIa) (Greenberg, C. S., et al., 1991, *FASEB J.* 5, 3071-3077) and keratinocyte TGase (Thacher, S. M. & Rice, R. H., 1985, *Cell* 40, 685-695), tTGases are calcium-dependent enzymes that catalyze the formation of crosslinks proteins via ε(γ-glutamyl) isopeptide bonds and the incorporation of polyamines at certain glutamine residues (Greenberg, C. S., et al., 1991, *FASEB J.* 5, 3071-3077).

However, tTGase is unique in the transglutaminase family of enzymes in that is able to bind and hydrolyze GTP and ATP (Achyuthan, K. B. & Greenberg, C. S., 1987, *J. Biol. Chem.* 262, 1901-1906), and to bind to fibronectin (Achyuthan, K. E., et al., 1995, *J. Immunol. Methods* 180, 67-79). The enzyme is predominantly located in the cytosol, although tTGase has also been reported to exist in the nucleus (Lesort, M., et al., 1998, *J. Biol. Chem.* 273, 11991-11994), at the cell surface and in the extracellular matrix (Martinez, J., et al., 1994, *Biochemistry* 33, 2538-2545). Tissue TGase is highly expressed in endothelial cells (Greenberg, C. S., et al., 1987, *Blood* 20, 702-709) and its activity at the surface of such cells is thought to enhance basement membrane stabilisation, cell spreading and cell adhesion (Martinez, J., et al., 1994, *Biochemistry* 33, 2538-2545, Greenberg, C. S., et al., 1987, *Blood* 20, 702-709, Kinsella, M. G. & Wight, T. N., 1990, *J. Biol. Chem.* 265, 17891-17896, Jones, R. A., et al., 1997, *J. Cell Sci.* 110, 2461-2472, Gaudry C. A., et al., 1999, *Exp. Cell Res.* 252, 104-113). However, the overall significance of the high amount of enzyme in this cell type and its biological function is poorly understood.

Antisense studies in the endothelial-like cell line ECV304 have demonstrated that tTGase-deficient cells exhibit severely impaired cell adhesion (Jones, R. A., et al., 1997, *J. Cell Sci.* 110, 2461-2472), and ECV304 cells transfected with a chimeric form of the enzyme that contains a Protein kinase Cε-epitope tag show strong tTGase staining at cell adhesion sites that co-distribute with the β1-integrin (Gaudry C. A., et al., 1999, *Exp. Cell Res.* 252, 104-113).

Recently, a study by Haroon et al (Haroon, Z. A., et al., 1999, *FASEB J.* 13, 1787-1795) has demonstrated that tTGase is expressed and active in rat dermal wound healing and angiogenesis. By examining biopsy punch wounds throughout the healing process, tTGase antigen and activity were observed at sites of neovascularisation and in the provision of fibrin matrix in the wound bed 24 hours after injury. Tissue TGase antigen levels increased four- to five-fold at three days after wounding and were ultimately degraded. In this study, it was also found that endothelial cells, macrophages and skeletal muscle cells express tTGase and that the addition of exogenous recombinant tTGase led to an increase in vessel length density.

On the basis of studies such as those by Haroon et al, which highlight a role of TGase in promoting angiogenesis, skilled persons have sought TGase inhibitors as therapeutic agents for inhibiting angiogenesis.

DETAILED DESCRIPTION OF THE INVENTION

A first aspect of the invention relates to use of a transglutaminase in the preparation of a medicament for inhibiting angiogenesis.

A second aspect of the invention provides a method of inhibiting angiogenesis in a subject comprising administering to said subject at least one transglutaminase in an amount sufficient to inhibit angiogenesis.

By 'a transglutaminase' we include a member of the group of enzymes identified by Enzyme Commission System of Classification No. 2.3.2.13 (EC 2.3.2.13).

In a preferred embodiment of the first and second aspects of the invention the transglutaminase is a tissue transglutaminase.

In an alternative embodiment, the transglutaminase is a plasma transglutaminase.

Preferably, the transglutaminase is prepared from mammalian tissue or cells.

More preferably, the transglutaminase is prepared from human tissue or cells. For example, the transglutaminase may be extracted from human tissue sources such as lung, liver, spleen, kidney, heart muscle, skeletal muscle, eye lens, endothelial cells, erythrocytes, smooth muscle cells, bone and macrophages. Advantageously, the transglutaminase is a tissue transglutaminase derived from human red cells (erythrocytes), or a plasma transglutaminase derived from either human placenta or human plasma.

Most preferably, the transglutaminase is a human tissue transglutaminase.

Alternatively, the transglutaminase may be obtained from a culture of human cells that express a mammalian transglutaminase, using cell culture methodology well known in the art. Preferred cell line sources of such transglutaminases include human endothelial cell line ECV304 (for tissue transglutaminase) and human osteosarcoma cell line MG63.

It will be appreciated by those skilled in the art that the determination of the dose of transglutaminase required to inhibit angiogenesis may be determined using a variety of techniques. For example, a number of conventional imaging methods, such as computed tomography (CT), magnetic resonance (MR) imaging, positron emission tomography (PET), and ultrasonography (US), that are ordinarily used to detect tumour mass can be adapted to focus on vascular features of tumours and other tissues. tissues. For example, blood flow, blood volume, permeability, vascular density, and metabolism are parameters anatomically and functionally associated with angiogenesis.

(i) CT Imaging
CT imaging can be performed with contrast agents to define the intravascular compartment, including blood flow, blood volume, mean fluid transit time, and capillary permeability (Miles & Kelley, 1997, *Br. J. Radiol.* 70:74-79). Functional CT techniques can delineate increases in tissue perfusion that may reflect malignancy, even when there is no gross anatomic abnormality present (Miles, 1999, *Eur. J. Radiol.* 30:198-205)).

(ii) US Imaging
US imaging can identity vascular features in tumours at different levels of resolution (40-200 μm-diameter vessels), depending on the technique employed. Contrast material-enhanced US with an intravascular agent can generate a blood flow, a blood volume, or a vascularity index within malignant tissue. Targeted imaging with ultrasound destruction of microbubbles may provide even further resolution of the tumour vascular tree (Cheng et al., 1999, *Cancer* 85:651-657). Colour flow Doppler US has been used to characterize tumour xenografts in mice (Lassau et al., 1999, *Invest, Radiol.* 34:194-198)) and solid tumours in patients (Cheng et al., 1999, *Cancer* 85:651-657; Cheng et al., 1998, *Cancer* 82:1881-1886).

(iii) MR Imaging
MR imaging can define both blood volume and blood vessel permeability by using dynamic enhancement of blood pool contrast agents. For example, use of gadopentetate dimeglumine can assist in distinguishing between normal (nonleaky) and malignant (leaky) tissues, reflecting the hyperpermeable tumour vasculature (Brasch et al., 1998, *Acad. Radiol.* 5(suppl. 1):S2-S5). In addition, contrast material uptake have been shown to correlate with microvessel density in experimental tumours (van Dijke et al., 1996, 198:813-818).

(iv) PET Imaging
PET imaging can be used to evaluate tumour metabolism, as well as blood flow and volume. A number of radiotracers, such as water with oxygen-15, carbon monoxide with carbon-11, and fluorodeoxy-glucose with fluorine-18, are available to characterise neoplastic tissue. For example, radiolabelled fluoromisonidazole has been used with PET to provide functional information about the results of antiangiogenic therapy (Rasey et al., 2000, *Radiol. Res.* 153:84-92).

Alternatively, novel imaging targets such as cell-surface integrins, endothelial apoptosis, angiopoietins, and the thermal and near-infrared signature of angiogenesis may be exploited for angiogenesis imaging.

(i) Targeting Integrins
Angiogenic endothelial cells express adhesion molecules possessing the Ar-Gly-Asp (RGD)-motif, known as the $\alpha_v\beta_3$ and $\alpha_v\beta_5$ integrins. Monoclonal antibodies directed against the $\alpha_v\beta_3$ integrin (LM609) have been covalently bound to paramagnetic liposomes to create a targeted imaging system capable of imaging tumour angiogenesis in a VX2 rabbit carcinoma with MR (Sipkins et al., 1998, *Nat. Med.* 4:623-626).

(ii) Imaging Endothelial Cell Apoptosis
Markers of cell endothelial cell apoptosis, such as annexin V, may be adapted for radiolabelling and imaging of an antiangiogenic effect of cancer therapy (Ravanat et al., 1992, *Biochem. J.* 282:7-13).

(iii) Vascular Stabilisation and Angiopoietins
The tumour vasculature, unlike healthy blood vessels, is heterogeneous and immature and lacks architecture stability. Selective imaging of either angiopoietin-1 (required for vascular stabilisation) or angiopoietin-2 (required for destabilisation), with use of covalently linked monoclonal antibodies to paramagnetic particles, may be used to localise and evaluate the state of the tumour vasculature.

(iv) Infrared Signature
Optical imaging with infrared and near-infrared sensors may also be used to assess tumour vascularity. The availability of high-resolution, military-grade and aerospace-grade infrared sensors, coupled to sensitive endothelial molecular markers, now enables detailed study of the infrared and hyperspectral signature characteristics of tumour angiogenesis. Near-infrared (0.8-2.0 μm wavelength) tomography can also provide a convenient, non-invasive imaging technique to monitor angiogenesis. This technique may be used to assess tumour vascularity by using a contrast agent such as absorption bands of oxy- and deoxybaemoglobin to estimate tumour blood flow and blood volume (Ntziachristos et al., 2000, *Proc. Natl. Acad. Sci. USA* 97:2767-2772).

Angiogenesis may also be measured using the following indirect techniques.

(i) Morphological Tests
Angiogenesis may be measured using immunohistochemical analysis of biopsy sample, e.g. immunostaining for Factor VIII, CD34, VEGF or bFGF (see Weidner et al, 1993, *Am. J. Pathol.* 143, 401-409 and Weider et al, 1991, *N. Engl. J. Med.* 324, 1-8).

(ii) Measurement of Biochemical Markers

Biochemical markers (e.g. VEGF, bFGF) in blood and urine samples may also be used to assess the level of angiogenesis (see Li et al, 1994, *Lancet* 344, 82-86; Nguyen et al, 1994, *J. Natl. Cancer Inst.* 86, 356-361; Watanabe et al, 1992, *Mol. Biol. Cell* 3, 324-330; Wu et at, 1997, In: *Human Circulating Tumour Markers: Current Concepts And Clinical Applications*, American Society of Clinical Pathologists, Chicago).

(iii) Imaging of Tumour Mass

Tumour mass may also be measured by conventional techniques, such as CT, MR and PET imaging, to provide an indirect measure of the dose of transglutaminase required to inhibit angiogenesis.

It will be appreciated by those skilled in the art that the source of the transglutaminase may be selected according to its intended use. For example, if it is to be used to inhibit angiogenesis in the vicinity of a solid tumour in the lungs, it may be beneficial for the transglutaminase to be a lung-derived transglutaminase.

In an alternative embodiment of the first and second aspects of the invention, the transglutaminase is a recombinant transglutaminase. For example, recombinant factor XIII production is described in European Patent Application No. EP 268 772 A.

Nucleic acid molecules encoding a transglutaminase are known in the art. For example, the coding sequence for human coagulation factor XIII A1 polypeptide is disclosed in Grundmann et al, 1986, *Proc. Natl. Acad. Sci. USA* 83(21), 8024-8028 (accession no. NM000129). The coding sequence for human tissue transglutaminase is disclosed in Gentile et al, 1991, *J. Biol. Chem.* 266(1) 478-483 (Accession no. M55153).

Nucleic acid molecules encoding a transglutaminase may be used in accordance with known techniques, appropriately modified in view of the teachings contained herein, to construct an expression vector, which is then used to transform an appropriate host cell for the expression and production of the polypeptide of the invention. Methods of expressing proteins in recombinant cells lines are widely known in the art (for example, see Sambrook et at, 1989, *Molecular Cloning, A Laboratory Manual*, Second Edition, Cold Spring Harbor, N.Y.). Exemplary techniques also include those disclosed in U.S. Pat. Nos. 4,440,859 issued 3 Apr. 1984 to Rutter et at, 4,530,901 issued 23 Jul. 1985 to Weissman, 4,582,800 issued 15 Apr. , 1986 to Crowl, 4,677,063 issued 30 Jun. 1987 to Mark et at, 4,678,751 issued 7 Jul. 1987 to Goeddel, 4,704,362 issued 3 Nov. 1987 to Itakura et al, 4,710,463 issued 1 Dec. 1987 to Murray, 4,757,006 issued 12 Jul. 1988 to Toole, Jr. et at, 4,766,075 issued 23 Aug. 1988 to Goeddel et at and 4,810,648 issued 7 Mar. 1989 to Stalker.

The nucleic acid molecule, e.g. cDNA, encoding the transglutaminase may be joined to a wide variety of other DNA sequences for introduction into an appropriate host The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. Thus, the DNA insert may be operatively linked to an appropriate promoter. Bacterial promoters include the *E. coli* lacI and lacZ promoters, the T3 and T7 promoters, the gpt promoter, the phage λ PR and PL promoters, the phoA promoter and the trp promoter. Eukaryotic promoters include the CMV immediate early promoter, the HSV thymidine kinase promoter, the early and late SV40 promoters and the promoters of retroviral LTRs. Other suitable promoters will be known to the skilled artisan. Alternatively, the Baculovirus expression system in insect cells may be used (see Richardson et al, 1995, *Methods in Molecular Biology* Vol 39, J Walker ed., Humana Press, Totowa, N.J.). The expression constructs will desirably also contain sites for transcription initiation and termination, and in the transcribed region, a ribosome binding site for translation (e.g. see WO 98/16643).

The vector is then introduced into the host through standard techniques. Generally, not all of the hosts will be transformed by the vector and it will therefore be necessary to select for transformed host cells. One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for such a selectable trait can be on another vector, which is used to co-transform the desired host cell.

Host cells that have been transformed by the recombinant DNA encoding the transglutaminase are then cultured for a sufficient time and under appropriate conditions known to those skilled in the art in view of the teachings disclosed herein to permit the expression of the transglutaminase, which can then be recovered.

The recombinant transglutaminase can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography (HPLC) is employed for purification.

Many expression systems are known, including systems employing: bacteria (e.g. *E. coli* and *Bacillus subtilis*) transformed with, for example, recombinant bacteriophage, plasmid or cosmid DNA expression vectors; yeasts (e.g. *Saccaromyces cerevisiae*) transformed with, for example, yeast expression vectors; insect cell systems transformed with, for example, viral expression vectors (e.g. baculovirus); plant cell systems transfected with, for example viral or bacterial expression vectors; animal cell systems transfected with, for example, adenovirus expression vectors.

The vectors include a prokaryotic replicon, such as the Col E1 ori, for propagation in a prokcaryote, even if the vector is to be used for expression in other, non-prokaryotic cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. Examples of an inducible mammalian expression vectors include pMSG, also available from Pharmacia (Piscataway, N.J., USA), and the tetracycline (tet) regulatable system, available form Clontech. The pMSG vector uses the glucocorticoid-inducible promoter of the mouse mammary tumor virus long terminal repeat to drive expression of the cloned gene. The tet regulatable system uses the presence or absence of tetracycline to induce protein expression via the tet-controlled transcriptional activator.

Useful yeast plasmid vectors are pRS403-406 and pRS413-416 and are generally available from Stratagene Cloning Systems (La Jolla, Calif. 92037, USA). Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

Methods well known to those skilled in the art can be used to construct expression vectors containing the coding sequence and, for example appropriate transcriptional or translational controls. One such method involves ligation via homopolymer tails. Homopolymer polydA (or polydC) tails are added to exposed 3' OH groups on the DNA fragment to be cloned by terminal deoxynucleotidyl transferases. The fragment is then capable of annealing to the polydT (or polydG) tails added to the ends of a linearised plasmid vector. Gaps left following annealing can be filled by DNA polymerase and the free ends joined by DNA ligase.

Another method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic molecules called linkers and adaptors. DNA fragments with blunt ends are generated by bacteriophage T4 DNA polymerase or *E. coli* DNA polymerase I which remove protruding 3' term and fill in recessed 3' ends. Synthetic linkers, pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one pre-formed cohesive end.

Synthetic linkers containing a variety of restriction endonuclease sites are commercially available from a number of sources including International Biotechnologies Inc, New Haven, Conn., USA.

A desirable way to modify the nucleic acid molecule encoding the transglutaminase is to use the polymerase chain reaction as disclosed by Saiki et al (1988) *Science* 239, 487-491. In this method the nucleic acid molecule, e.g. DNA, to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Conveniently, the mammalian transglutamninase is a variant transglutaminase.

By "a variant" we include a polypeptide comprising the amino acid sequence of a naturally occurring mammalian transglutaminase wherein there have been amino acid insertions, deletions or substitutions, either conservative or non-conservative, such that the changes do not substantially reduce the activity of the variant compared to the activity of the activated naturally occurring mammalian transglutaminase. For example, the variant may have increased angiogenesis inhibiting activity compared to the activity of the naturally occurring transglutaminase.

Alternatively, the variant may have increased stability, e.g. tolerance to proteases, pH and thermal stability, thereby increasing longevity (i.e. active half-life) of the enzyme at site of action.

Advantageously, the variant mammalian transglutaminase is a fragment of a naturally occurring tissue transglutaminase, said fragment retaining substantially the same angiogenesis inhibiting activity as the naturally occurring transglutaminase.

Variant transglutaminases may be made using methods of protein engineering and site-directed mutagenesis commonly known in the art (for example, see Sambrook et al (1989) *Molecular Cloning, A Laboratory Manual*, Second Edition, Cold Spring Harbor, N.Y.).

In a preferred embodiment of the first and second aspects of the invention, the transglutaminase is a variant transglutaminase which is targeted to a target cell population (e.g. a tumour).

Preferably, the transglutaminase is a fusion protein comprising a target cell specific portion and a transglutaminase portion having angiogenesis inhibiting activity. By "fusion protein" we include a protein comprising one or more functionally distinct portions, wherein the distinct portions are contained within a single polypeptide chain produced by recombinant DNA techniques.

Preferably, the target-cell specific portion and the transglutaminase portion are separated by a linker sequence, for example to allow greater flexibility of the portions relative to one another. Alternatively, the target-cell specific and the transglutaminase portion are separate moieties linked together by any of the conventional ways of cross-linking polypeptides, such as those generally described in O'Sullivan et al *Anal. Biochem.* (1979) 100, 100-108. For example, the antibody portion may be enriched with thiol groups and the enzyme portion reacted with a bifunctional agent capable of reacting with those thiol groups, for example the N-hydroxysuccinimide ester of iodoacetic acid (NHIA) or N-succinimidyl-3-2-pyridyldithio)propionate (SPDP). Amide and thioether bonds, for example achieved with m-maleimidobenzoyl-N-hydroxysuccinimide ester, are generally more stable in vivo than disulphide bonds.

By "target cell-specific portion" we mean a portion of the fusion protein which comprises one or more binding sites which recognise and bind to entities on a target cell.

The entities recognised by the target cell-specific portion are expressed predominantly, and preferably exclusively, on the said target cell. The target cell specific portion may contain one or more binding sites for different entities expressed on the same target cell type, or one or more binding sites for different entities expressed on two or more different target cell types.

Preferably, the target cell-specific portion recognises the target cell with high avidity.

By "high avidity" we mean that the target cell-specific portion recognises the target cell with a binding constant of at least $K_d=10^{-6}M$, preferably at least $K_d=10^{-9}M$, suitably $K_d=10^{-10}M$, more suitably $K_d=10^{-11}M$, yet more suitably still $K_d=10^{-12}M$, and more preferably $K_d=10^{-15}M$ or even $K_d=10^{-18}M$.

The entity which is recognised may be any suitable entity which is expressed by tumour cells, immune cells, etc, but which is not expressed, or at least not with such frequency, in cells which one does not wish to target. The entity which is recognised will often be an antigen. Examples of antigens include those listed in Table 1.

TABLE 1

1. Tumour Associated Antigens

| Antigen | Antibody | Existing Uses |
|---|---|---|
| Carcino-embryonic Antigen | C46 (Amersham) 85A12 (Unipath) | Imaging & Therapy of colon/rectum tumours. |
| Placental Alkaline Phosphatase | H17E2 (ICRF, Travers & Bodmer) | Imaging & Therapy of testicular and ovarian cancers. |
| Pan Carcinoma | NR-LU-10 (NeoRx Corporation) | Imaging & Therapy of various carcinomas incl. small cell lung cancer. |
| Polymorphic Epithelial Mucin (Human milk fat globule) | HMFG1 (Taylor-Papadimitriou, ICRF) (Antisoma plc) | Imaging & Therapy of ovarian cancer, pleural effusions, breast, lung & other common epithelial cancers. |
| Human milk mucin core protein | SM-3(IgG1)[1] | Diagnosis, Imaging & Therapy of breast cancer |
| β-human Chorionic Gonadotropin | W14 | Targeting of enzyme (CPG2) to human xenograft choriocarcinoma in nude mice. (Searle et al (1981) Br. J. Cancer 44, 137-144) |
| A Carbohydrate on Human Carcinomas | L6 (IgG2a)[2] | Targeting of alkaline phosphatase. (Senter et al (1988) Proc. Natl. Acad. Sci. USA 85, 4842-4846 |
| CD20 Antigen on B Lymphoma (normal and neoplastic) | 1F5 (IgG2a)[3] | Targeting of alkaline phosphatase. (Senter et al (1988) Proc. Natl. Acad. Sci. USA 85, 4842-4846 |

[1]Burchell et al (1987) Cancer Res. 47, 5476-5482
[2]Hellström et al (1986) Cancer Res. 46, 3917-3923
[3]Clarke et al (1985) Proc. Natl. Acad. Sci. USA 82, 1766-1770

Other antigens include alphafoetoprotein, Ca-125, prostate specific antigen and members of the epidermal growth factor receptor family, namely EGFR, erb B2 (e.g. Herceptin antibody), erb B3 and erb B4.

2. Immune Cell Antigens

| Antigen | Antibody | Existing Uses |
|---|---|---|
| B-lymphocyte Surface Antigen (CD22) | RFB4 (Janossy, Royal Free Hospital) | Immunotoxin therapy of B cell lymphoma. |
| Pan T lymphocyte | H65 (Bodmer, | Immunotoxin |

-continued

| Antigen | Antibody | Existing Uses |
|---|---|---|
| Surface Antigen (CD5) | Knowles ICRF, Licensed to Xoma Corp., USA) | treatment of Acute Graft versus Host disease, Rheumatoid Arthritis. |

In a preferred embodiment, the target cell specific portion recognises and selectively binds to a tumour cell antigen.

Conveniently, the target cell-specific portion comprises two or more binding sites for the target cell, for example the target cell-specific portion may be an antibody or bivalent fragment thereof. Said target cell-specific portion may have respective 'arms' that recognise the same entity as one another or that recognise different entities.

Preferably the target cell specific portion is a bivalent antibody or fragment thereof, e.g. F(ab')$_2$ fragments. By "bivalent" we mean that the said antibody and F(ab')$_2$ fragment has two antigen combining sites. In contrast, Fab, Fv, ScFv, disulphide Fv and dAb fragments are monovalent, having only one antigen-binding site.

More preferably, the target cell specific portion is bivalent and comprises two or more different binding sites for the target cell.

The different binding sites for the target cell may or may not be two or more different antibodies, or fragments thereof, which are directed to different entities expressed on the target cell. Alternatively, the different binding sites for the target cell may recognise and selectively bind the cell in some other, non-immune sense.

A further alternative is that one or more of the binding sites is an antibody, or part thereof, and that one or more of the binding sites for the target cell recognise and selectively bind the cell in some other, non-immune sense.

A compound which has binding sites for two or more target cell-specific entities may be more specific for binding to the said target cell, and a compound which has more than one of each of the different binding sites may bind to the said target cell with greater avidity. In combining two or more binding sites, which in themselves may be of high specificity but low affinity, it will be possible to generate in the compound of the invention a higher affinity for the target cell whilst retaining the specificity of the binding sites. For example, one 'arm' of the target cell-specific portion may recognise molecules on cell types I, II and III, whereas the other 'arm' may recognise molecules on cell types I, IV and V. Thus, transglutaminase fusion protein comprising such a target cell-specific portion will have greater specificity for cell type I compared with cell types II, III and IV. This aspect of the invention is particularly useful, as there have been very few completely target cell-specific molecules discovered, whereas molecules which occur on a few cell types, and which are useful in this aspect of the invention, are well known. Such molecules are usually cell-surface antigens for which cross-reactive antibodies are known. Examples of such molecules are given in Table 2.

TABLE 2

| Antigen | Cell-type | Antibody |
|---|---|---|
| CD9 | Pre-B cells, monocytes, platelets | MM2/57 (IgG2b, mouse) |
| CALLA | Lymphoid progenitor cells, granulocytes | B-E3 (IgG2a, mouse) |
| CD13 | Myeloid monocytes, granulocytes | B-F10 (IgG1, mouse) |

TABLE 2-continued

| Antigen | Cell-type | Antibody |
|---|---|---|
| CD24 | B-cells, granulocytes | ALB-9 (IgG1, mouse) |
| CD61 | Platelets, megakaryocytes | PM 6/13 (IgG1, mouse) |

The antibodies described in Table 2 are generally available from Serotec, Oxford, OX5 1BR, UK.

Monoclonal antibodies that bind to many of the antigens listed in Table 1 are already known, but, in any case, with presently available techniques in relation to monoclonal antibody technology, antibodies can be prepared to most antigens. For example, suitable monoclonal antibodies to selected antigens may be prepared by known techniques, for example those disclosed in *Mononoclonal Antibodies: A manual of techniques*, H Zola (CRC Press, 1988) and in *Monoclonal Hybridoma Antibodies: Techniques and Applications*, J G R Hurrell (CRC Press, 1982) and *Antibody Engineering, A Practical Approach*, McCafferty, J. et al, ed. (IRL Press, 1996).

Preferably, the target cell specific portion is an antibody or antigen-binding fragment thereof. More preferably, the target cell specific portion is a monoclonal antibody or antigen-binding fragment thereof. Antigen-binding antibody fragments include Fab-like molecules (Better et al (1988) *Science* 240, 1041); Fv molecules (Skerra et al (198) *Science* 240, 1038); disulphide-linked Fv molecules (Young et al, 1995, *FEBS Lett.* 377:135-139); single-chain Fv (ScFv) molecules where the $V_H$ and $V_L$ partner domains are linked via a flexible oligopeptide (Bird et at (1988) *Science* 242, 423; Huston et al (1988) *Proc. Natl. Acad. Sci. USA* 85, 5879) and single domain antibodies (dAbs) comprising isolated V domains (Ward et at (1989) *Nature* 341, 544). A general review of the techniques involved in the synthesis of antibody fragments which retain their specific binding sites is to be found in Winter & Milstein (1991) *Nature* 349, 293-299.

Preferably, the target cell-specific portion is or comprises a Fab or F(ab')$_2$ molecule. Alternatively, the target cell-specific portion is or comprises a scFv molecule.

In a preferred embodiment, the target cell specific portion is a humanised monoclonal antibody or antigen-binding fragment thereof. By "humanised monoclonal antibody" we include monoclonal antibodies having at least one chain wherein the framework regions are predominantly derived from a first, acceptor monoclonal antibody of human origin and at least, one complementarity-determining region (CDR) is derived from a second, donor monoclonal antibody. The donor monoclonal antibody may be of human or non-human origin, for example it way be a murine monoclonal antibody.

Methods of making humanised monoclonal antibodies are well-known in the art, for example see Jones et al (1986) *Nature* 321:522-525, Riechmann et al (1988) *Nature* 332: 323-327, Verhoeyen et al (1988) *Science* 239:1534-1536 and EP 239 400 (to Winter). Humanised, or chimeric, antibodies are also discussed by Neuberger et al (1988, 8*th International Biotechnology Symposium* Part 2, 792-799).

Tissue transglutaminase has high affinity for fibronectin. Any enzyme released into the blood would be found bound to fibronectin and could be detected as a complex. Any increase in crosslinking in a particular tissue would eventually lead to gradual breakdown of the matrix by proteases e.g. metalloproteinases etc. The ε (γ-glutamyl) lysine dipeptide crosslink is resistant to proteases and would be released into the serum as the free isopeptide. Increase in crosslinking in a tissue is therefore likely to lead to release of the free isopeptide into the serum which is detectable by RP-HPLC or cation exchange chromatography (see Griffin M and Wilson J, 1984, *Mol. Cell Biochem.* 58, 37-49).

In a preferred embodiment of the first and second aspects of the invention, the transglutaminase is for killing a target population of cells in a mammal. Cell death is accomplished by inhibiting angiogenesis in the vicinity of the target population of cells, such that the blood vessels needed to support and sustain said cells are prevented from forming. This approach may be particularly effective when the target population of cells is growing rapidly, for example in solid tumours. Data indicate that addition of TGase to the angiogenesis assay results in a highly crosslinked matrix which prevents angiogenesis, e.g. by blocking cell migration of endothelial cells and by blocking organised endothelial cell basement membrane formation.

Preferably, the medicament is for treating cancer, especially cancers manifesting themselves as solid tumours. Thus, further aspects of the present invention provide the use of a transglutamninase in the preparation of a medicament for treating cancer and a method of treating cancer in a subject comprising administering to said subject at least one transglutaminase in an amount sufficient to induce tumour cell death and/or tumour regression.

Alternatively, the medicament is for treating rheumatoid arthritis. Conveniently, the medicament is for treating psoriasis. Suitably, the medicament is for treating retinopathy.

It will be appreciated by those skilled in the art that the transglutaminase of the first or second aspect of the invention may be administered by any route known or developed in the art. Thus, it may be administered by parenteral injection (e.g. intravenous, subcutaneous or intramuscular), by inhalation or nasal administration, or possibly orally.

Preferably, the transglutaminase is administered systemically, for example intravenously. Alternatively, the transglutaminase is administered topically, i.e. at or near a target site where angiogenesis is to be inhibited. Advantageously, the transglutaminase is administered into the feeder arteries of the tumour or other cell population to be killed.

Treatment with the transglutaminase according to the invention may consist of a single dose or a plurality of doses over a period of time. Advantageously, the transglutaminase is administered repeatedly.

Proteins and peptides such as transglutaminases may also be delivered using an injectable sustained-release drug delivery system. These are designed specifically to reduce the frequency of injections. An example of such a system is Nutropin Depot which encapsulates recombinant human growth hormone (rhGH) in biodegradable microspheres that, once injected, release rhGH slowly over a sustained period.

Alternatively, the transglutaminase can be administered by a surgically implanted device that releases the transglutaminase directly to the required site. For example, Vitrasert releases ganciclovir directly into the eye to treat CMV retinitis. The direct application of this toxic agent to the site of disease achieves effective therapy without the drug's significant systemic side-effects.

Transglutaminases can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs (e.g. proteins/peptides) or genes or can simply act as "bullets" that generate pores in the skin through which the drugs can enter.

An alternative method of transglutaminase delivery is the ReGel injectable system that is thermo-sensitive. Below body temperature, ReGel is an injectable liquid while at body temperature it immediately forms a gel reservoir that slowly erodes and dissolves into known, safe, biodegradable polymers. The active drug, in the present case transglutaminase, is delivered over time as the biopolymers dissolve.

Protein and peptide pharmaceuticals can also be delivered orally. The process employs a natural process for oral uptake of vitamin $B_{12}$ in the body to co-deliver proteins and peptides. By riding the vitamin $B_{12}$ uptake system, the protein or peptide can move through the intestinal wall. Complexes are synthesised between vitamin $B_{12}$ analogues and the drug that retain both significant affinity for intrinsic factor (IF) in the vitamin B12 portion of the complex and significant bioactivity of the drug portion of the complex.

It will be appreciated that a subject treated using the method according to the second aspect of the invention may be any mammal. Preferably, the subject is human. Alternatively, the subject is a dog, cat, horse, or other domestic or farm mammalian animal.

In a preferred embodiment of the second aspect of the invention, the subject has cancer. In alternative embodiments, the subject has rheumatoid arthritis or psoriasis.

A third aspect of the invention provides a composition comprising a transglutaminase in an amount sufficient to inhibit angiogenesis.

Preferably, the composition comprises a transglutaminase in an amount sufficient to produce a transglutaminase concentration of 50 µg/ml to 16 mg/ml in the region where angiogenesis is to be inhibited, e.g. near the solid tumour.

In a preferred embodiment of the second aspect of the present invention, the transglutaminase is administered using a gene therapy system. Thus, a nucleic acid molecule (polynucleotide encoding a transglutaminase is delivered into target cells (e.g. cancer cells) whereupon it is expressed to produce an active transglutaminase protein. It will be appreciated by persons skilled in the art that any of the methods of gene therapy known in the art may be utilised (for reviews see Lemoine and Cooper (Eds.), 1996, *Gene Therapy*, BIOS Science Publications; Scientific American, June 1997, Special Edition on Gene Therapy pp 79-103; Rosenberg (Ed.), 2000, '*Principles Practice of Gene Therapy*', In: *Biologic Therapy of Cancer*, pp 733-823, Lippincot Williams and Wilkins).

It will be appreciated that nucleic acid molecules encoding a transglutaminase may be operably linked to other nucleic acid sequences to enable efficient delivery to the target cells. Typically, the nucleic acid molecule encoding a transglutaminase is operatively linked to a promoter, which can induce expression of the transglutaminase in the target cell. Such promoters may be selected so as to target expression to particular cells, for example tissue specific promoters may be used. In a preferred embodiment, the target cells are tumour cells. Alternatively, the target cells may be cells in the vicinity of cells to be destroyed, for example the target cells may be fibroblasts located around tumours.

Examples of target cell specific promoters (tissue specific and tumour specific) for use in gene therapy are shown in Table 4.

TABLE 4

| Promoter | Specificity |
|---|---|
| (A) Tissue specific | |
| Prostate-specific antigen (kallikrein 2) | Prostate/prostate cancer |
| Tyrosinase | Melanocytes/melanoma |
| Albumin, hepatitis B virus core promoter | Liver/hepatoma |
| Growth hormone | Pituitary/pituitary cancer |
| Osteocalcin | Bone/osteosarcoma |
| Myelin basic protein, glial Fibrillary acidic protein | Glial cells/gliobalstoma multi-forme |
| Thyroglobulin | Thyroid/thyroid cancer |
| CD11 | Leukocytes/lymphoma |
| B-casein | Mammary/breast cancer |
| Surfactant | Bronchoalveolar/lung cancer |
| mck cells/rhabdomyosarcoma | Mygenic |
| kdr, tir, e-selectin | Endothelial cells/tumour vasculature |
| (B) Tumour specific | |
| α-fetoprotein | Oncofetal/hepatoma |
| Carcinoembryonic antigen | Oncofetal/colon cancer |
| MUC-1 | MUC-1 producing tumours |
| erbB-1 | erbB2 expressing tumours |
| grp 78/BiP | Stress inducible glucose regulated/tumour specific |
| pax 3 DNA binding, site prs-9 | Alveolar rhabdosarcoma |
| Secretory leukoprotease inhibitor | Carcinoma |
| Hexokinase type II | Glycolyis regulator/tumour-specific |

Preferably, the nucleic acid molecule (e.g. cDNA, genomic DNA or mRNA) is adapted for delivery to a human cell.

In accordance with the invention, nucleic acid molecules encoding a transglutaminase may be administered systemically by any effective route. For example, the nucleic acid molecule may be administered parenterally (e.g. intravenously, subcutaneously, intramuscularly) or by oral, nasal or other means which permit the molecule to access the target cells on the subject to be treated.

Alternatively the efficacy of the gene therapy embodiment of the present invention may be enhanced by limiting the availability of the nucleic acid molecule encoding a transglutaminase to its intended locus in vivo, permitting lower dosages to be used and minimising systemic effects.

Thus, the nucleic acid molecule encoding a transglutaminase may be applied locally to achieve the desired effect. In this way, the concentration of the nucleic acid molecule at the desired locus is much higher than if the molecules were administered systemically, and the therapeutic effect can be achieved using a significantly lower total amount. For example, it may be desirable to locally perfuse a tumour with the suitable delivery vehicle comprising the nucleic acid molecule encoding a transglutaminase for a period of time; additionally or alternatively the nucleic acid molecule may be injected directly into accessible tumours.

Means and methods of introducing a nucleic acid construct into a cell in a human or animal body are known in the art. Such delivery systems can be broadly divided into two types, viral and non-viral systems.

A number of suitable viral vectors for gene therapy have been developed, including vectors based on retroviruses, adenoviruses, herpes simplex virus, HIV and lentiviruses.

In a preferred embodiment, the nucleic acid molecule encoding a transglutaminase may be introduced into the target cells using retrovirus vectors, so that the construct is inserted into the genome of the tumour cell. For example, in Kuriyama et al (1991) *Cell Struc. and Func.* 16, 503-510 purified retroviruses are administered. Retroviruses provide a potential means of selectively infecting target cells such as cancer cells because they can only integrate into the genome of dividing cells; most normal cells surrounding cancers are in a quiescent, non-receptive stage of cell growth or, at least, are dividing much less rapidly than the tumour cells. Retroviral DNA constructs which encode a transglutaminase may be made using methods well known in the art. To produce active retrovirus it is usual to use an ecotropic psi2 packaging cell line grown in Dulbecco's modified Eagle's medium (DMEM) containing 10% foetal calf serum (FCS). Transfection of the cell line is conveniently achieved by calcium phosphate co-precipitation, and stable transformants are selected by addition of G418 to a final concentration of 1 mg/ml (assuming the retroviral construct contains a neo$^R$ gene). Independent colonies are isolated and expanded and the culture supernatant removed, filtered through a 0.45 μm pore-size filter and stored at −70° C. For the introduction of the retrovirus into the tumour cells, it is convenient to inject directly retroviral supernatant to which 10 μg/ml Polybrene has been added. For tumours exceeding 10 mm in diameter it is appropriate to inject between 0.1 ml and 1 ml of retroviral supernatant; preferably 0.5 ml.

Alternatively, cells which produce retroviruses may be injected into the target cells, as described in Culver et al (1992) *Science* 256, 1550-1552. The retrovirus-producing cells so introduced are engineered to actively produce retroviral vector particles so that continuous productions of the vector occurred within the tumour mass in situ. Thus, proliferating tumour cells can be successfully transduced in vivo if mixed with retroviral vector-producing cells.

Targeted retroviruses are also available for use in the invention; for example, sequences conferring specific binding affinities may be engineered into pre-existing viral env genes (see Miller & Vile, 1995, *FASEB J.* 9, 190-199 for a review of this and other targeted vectors for gene therapy).

Other methods for delivery of the transglutaminase encoding nucleic acid molecule to target cells include adenoviruses carrying external DNA via an antibody-polylysine bridge (see Curiel *Prog. Med. Virol.* 40, 1-18) and transferrin-polycation conjugates as carriers (Wagner et al (1990) *Proc. Natl. Acad. Sci. USA* 87, 3410-3414).

In the first of these methods, a polycation-antibody complex is formed with the nucleic acid molecule, wherein the antibody is specific for either wild-type adenovirus or a variant adenovirus in which a new epitope has been introduced which binds the antibody. The polycation moiety binds the nucleic acid via electrostatic interactions with the phosphate backbone. The adenovirus, because it contains unaltered fibre and penton proteins, is internalised into the cell and carries into the cell with it the nucleic acid (e.g. DNA) construct encoding the transglutaminase. It is preferred if the polycation is polylysine.

The nucleic acid molecule encoding the transglutaminase may also be delivered using adenovirus vectors, wherein the molecule is present within the adenovirus particle. In such methods, a high-efficiency nucleic acid delivery system is employed that uses receptor-mediated endocytosis to carry nucleic acid macromolecules into cells. This is accomplished by conjugating the iron-transport protein transferrin to polycations that bind nucleic acids. Human transferrin or the chicken homologue conalbumin (or combinations thereof) is covalently linked to the small DNA-binding protein protamine or to polylysines of various sizes through a disulphide linkage. These modified transferrin molecules maintain their ability to bind their cognate receptor and to mediate efficient iron transport into the cell. The transferrin-polycation molecules form electrophoretically stable complexes with DNA constructs or other genetic constructs of the invention independent of nucleic acid size (from short oligonucleotides to DNA of 21 kilobase pairs). When complexes of transferrin-polycation and the DNA constructs or other genetic constructs encoding a transglutaminase are supplied to the tumour cells, a high level of expression from the construct in the cells is achieved.

High-efficiency receptor-mediated delivery of nucleic acid molecules to target cells may also be achieved using the endosome-disruption activity of defective or chemically inactivated adenovirus particles produced by the methods of Cotten et al (1992) *Proc. Natl. Acad. Sci. USA*. 89, 6094-6098). This approach appears to rely on the fact that adenoviruses are adapted to allow release of their DNA from an endosome without passage through the lysosome, and in the presence of, for example transferrin linked to the DNA construct or other genetic construct of the invention, the construct is taken up by the cell by the same route as the adenovirus particle. The advantages of such an approach include that there is no need to use complex retroviral constructs; there is no permanent modification of the genome as occurs with retroviral infection; and the targeted expression system is coupled with a targeted delivery system, thus reducing toxicity to other cell types.

A further suitable vector for delivery of nucleic acid molecules encoding a transglutaminase to target cells is the disabled infectious single cycle (DISC) herpes simplex virus, as described by Boursnell et al, 1998, *Adv. Exp. Med. Biol.* 451:379-84. The advantage of DISC HSV is that it enables gene delivery without cell-to-cell spread or production of infectious progeny.

Alternative targeted delivery systems are also known, such as the modified adenovirus system described in WO 94/10323 wherein, typically, the DNA is carried within the adenovirus, or adenovirus-like, particle. Michael et al (1995) *Gene Therapy* 2, 660-668 describes modification of adenovirus to add a cell-selective moiety into a fibre protein. Mutant adenoviruses which replicate selectively in p53-deficient human tumour cells, such as those described in Bischoff et al. (1996) *Science* 274, 373-376 are also useful for delivering the genetic constructs to a cell.

More recently, promising results in gene transfer to the cells and tissues of nervous system have been obtained using the LentiVector® technology developed by Oxford Biomedica (WO 98/17816, WO 99/32646). These vectors are based on the equine infectious anaemia virus (EIAV), and unlike retroviral vectors are able to function in non-dividing or slowly-dividing cells.

Other suitable viruses or virus-like particles include adeno-associated viruses (AAV), vaccinia and parvovirus.

It will be appreciated by persons skilled in the art that "naked nucleic acid" and nucleic acid molecules complexed with cationic and neutral lipids may also be useful in the present invention. Suitable non-viral approaches to gene therapy are described in Ledley (1995) *Human Gene Therapy* 6, 1129-1144.

The nucleic acid molecule encoding a transglutaminase may be delivered to the locus by any means appropriate for localised administration of a drug. For example, a solution of the nucleic acid molecule can be injected directly to the site or can be delivered by infusion using an infusion pump. The nucleic acid molecule can also be incorporated into an implantable device which, when placed at the desired site, permits release of the nucleic acid molecule into the surrounding locus.

Alternatively, nucleic acid molecules may be administered via a hydrogel material. The hydrogel is non-inflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10% to about 80% by weight ethylene oxide and from about 20% to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the nucleic acid molecules are admixed into the liquid to a concentration of about 1 mg oligonucleotide per gram of hydrogel. The resulting mixture then is applied onto the surface to be treated, for example by spraying or painting during surgery or using a catheter or endoscopic procedures. As the polymer warns, it solidifies to form a gel, and the nucleic acid molecules diffuse out of the gel into the surrounding cells over a period of time defined by the exact composition of the gel.

Additionally, the nucleic acid molecule may be administered by means of other implants that are commercially available or described in the scientific literature, such as liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the nucleic acid molecules. The molecules can be incorporated into the material as it is polymerised or solidified, using melt or solvent evaporation techniques, or mechanically mixed with the material. In one embodiment, the nucleic acid molecules are mixed into or applied onto coatings for implantable devices such as dextran coated silica beads, stents, or catheters.

Other suitable methods involve simple delivery of the nucleic acid molecule into the cell for expression therein either for a limited time or, following integration into the genome, for a longer time. An example of the latter approach includes (preferably tumour-cell-targeted) liposomes (Nassander et al (1992) *Cancer Res.* 52, 646-653). For example, immunoliposomes (antibody-directed liposomes) are especially useful in targeting to cancer cell types which overexpress a cell surface protein for which antibodies are available. For the preparation of immuno-liposomes MPB-PE (N-[4-(p-maleimidophenyl)butyryl]-phosphatidylethanolamine) is synthesised according to the method of Martin & Papahadjopoulos (1982) *J. Biol. Chem.* 257, 286-288. MPB-PE is incorporated into the liposomal bilayers to allow a covalent coupling of the antibody, or fragment thereof, to the liposomal surface. The liposome is conveniently loaded with the nucleic acid encoding a transglutaminase for delivery to the target cells, for example, by forming the said liposomes in a solution of the DNA or other genetic construct, followed by sequential extrusion through polycarbonate membrane filters with 0.6 µm and 0.2 µm pore size under nitrogen pressures up to 0.8 MPa. After extrusion, the entrapped nucleic acid construct is separated from free nucleic acid molecules by ultracentrifugation at 80 000×g for 45 min. Freshly prepared MPB-PE-liposomes in deoxygenated buffer are mixed with freshly prepared antibody (or fragment thereof) and the coupling reactions are carried out in a nitrogen atmosphere at 4° C. under constant end over end rotation overnight. The immunoliposomes are separated from unconjugated antibodies by ultracentrifugation at 80 000×g for 45 min. Immuno-liposomes may be injected intraperitoneally or directly into the tumour.

A fourth aspect of the invention provides a pharmaceutical formulation comprising a composition according to the third aspect of the invention and a pharmaceutically acceptable carrier.

By 'pharmaceutically acceptable carrier' we include a substantially non-toxic, pyrogen-free excipient or adjuvant.

The formulations may conveniently be presented in unit dosage form and may be prepared by any of the methods well known in the art of pharmacy. Such methods include the step of bringing into association the active ingredient (i.e. the composition comprising a transglutaminase) with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention-suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. It will be appreciated by those skilled in the art that the transglutaminase for oral administration should preferably be formulated so as to be protected in the gut and to permit bioadsorption (see above).

Formulations suitable for parenteral administration include aqueous and non-aqueous sterile injection solutions which may contain anti-oxidants, buffers, bacteriostats and solutes which render the formulation isotonic with the blood of the intended recipient and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient.

Preferred, non-limiting examples which embody certain aspects of the invention will now be described, with reference to the following figures:

(A) shows mean tumour size ($cm^2$) over time. In the case of animals which developed multiple tumours, the tumour size for that animal was taken as the sum total size of all tumours found on the animal. When any individual tumour exceeded 1 $cm^2$ in size, the animal was sacrificed, however the terminal tumour size measurement for that animal was included in subsequent time points so as not to distort the mean tumour size.

(B) shows the change in individual tumour size ($cm^2$) over time. As stated above, animal were sacrificed when any individual tumour exceeded 1 $cm^2$ in size (indicated by asterisk).

Figure 10:
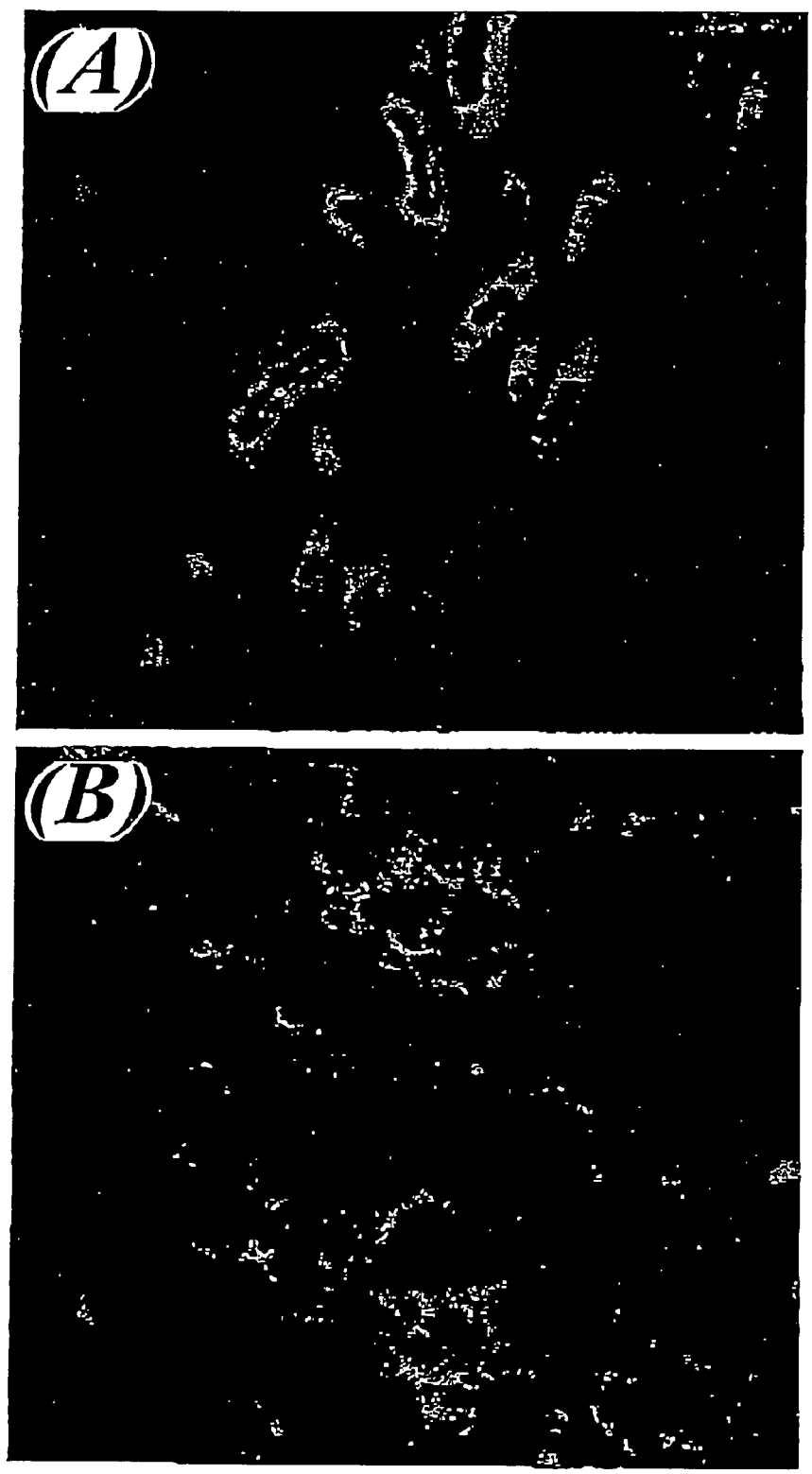

FIGS. 10 A and B demonstrates the effect of TGase treatment on staining for von Willebrand factor in CT26 mmour sections (magnification ×40).

Figure 11:
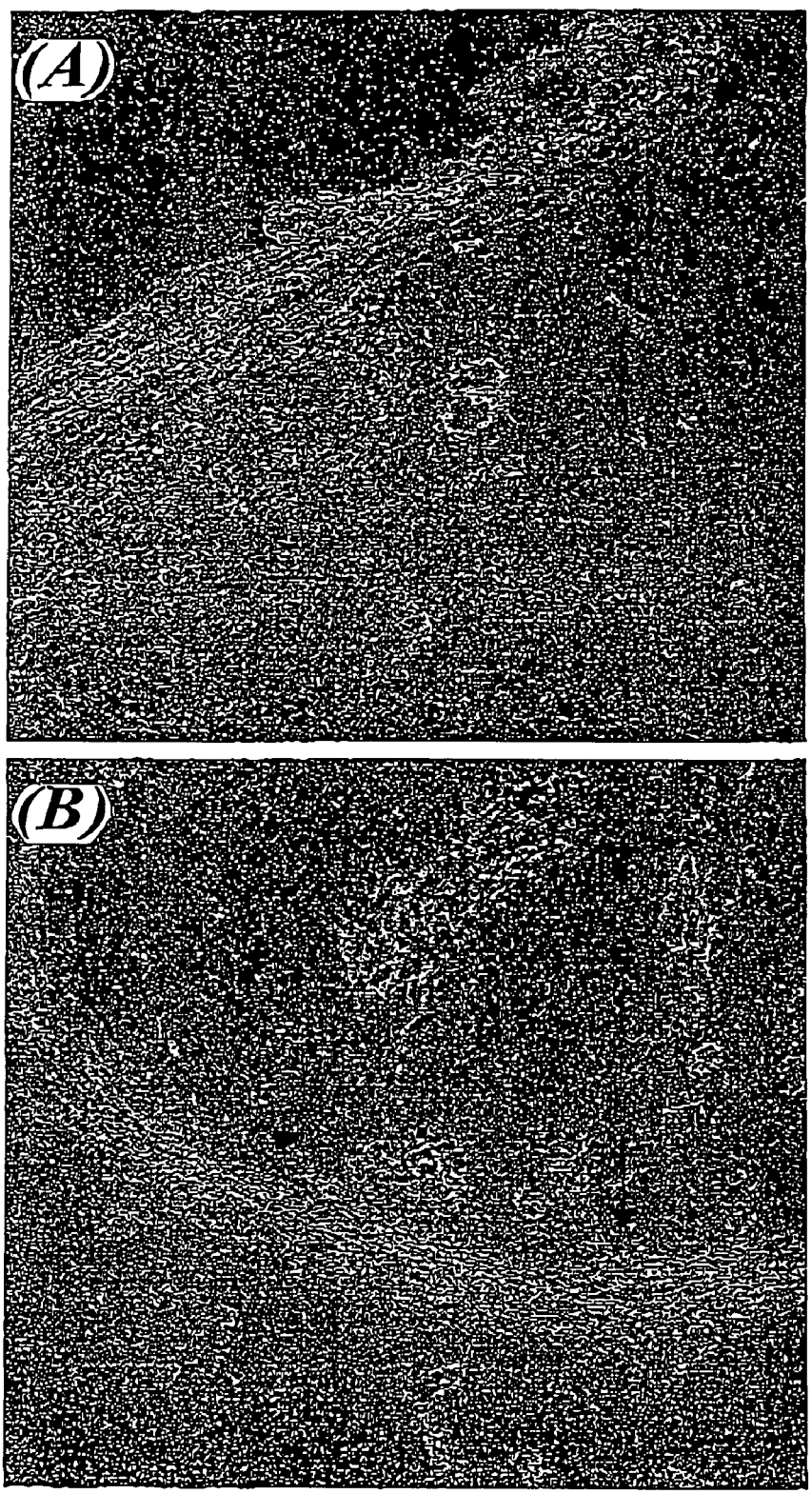

FIGS. 11 A and B demonstrates the effect of TGase treatment on staining for type I collagen in CT26 tumour sections (magnification ×10).

Figure 12:
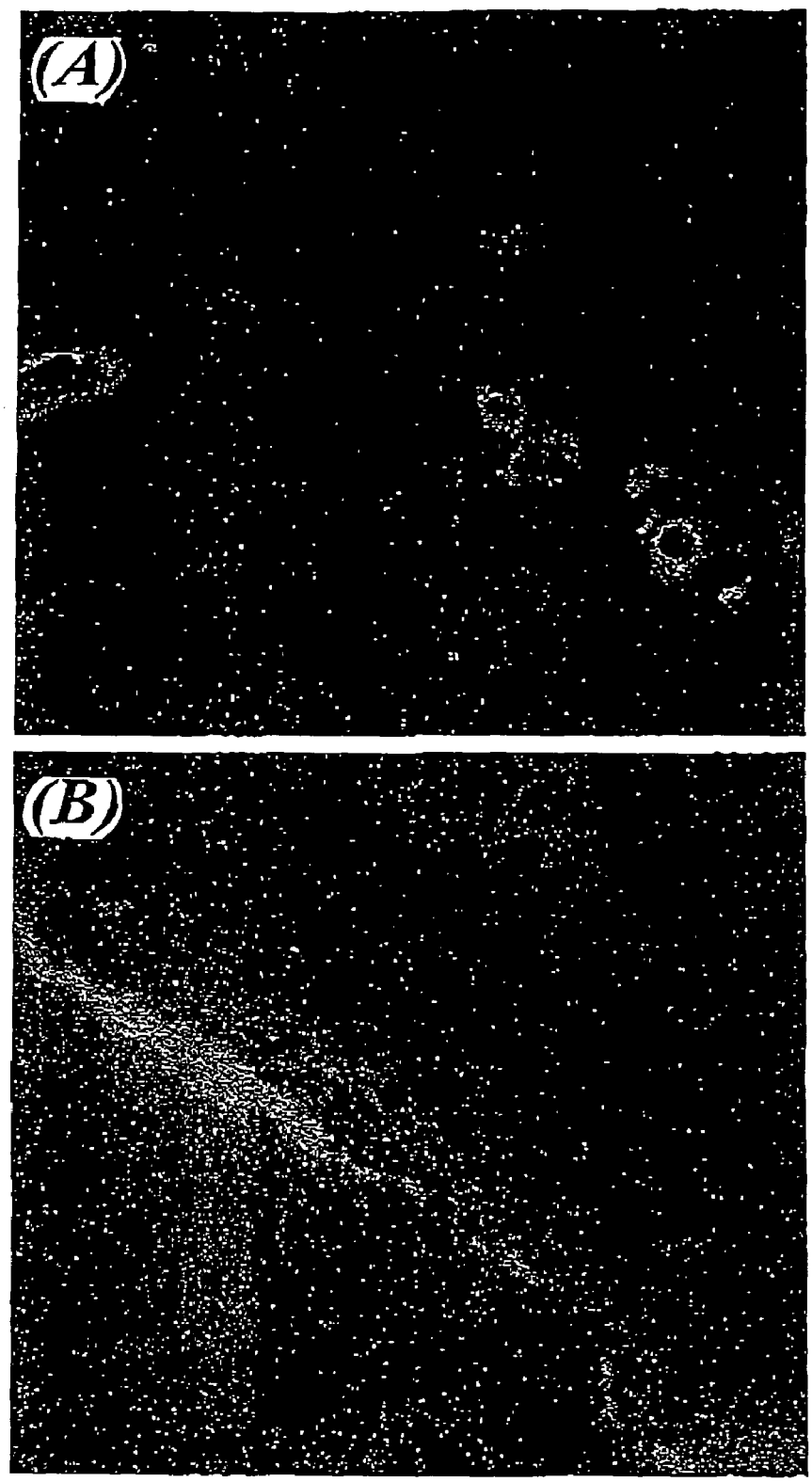

FIGS. 12 A and B demonstrates the effect of TGase treatment on staining for type III collagen in CT26 tumour sections (magnification ×40).

Figure 13:
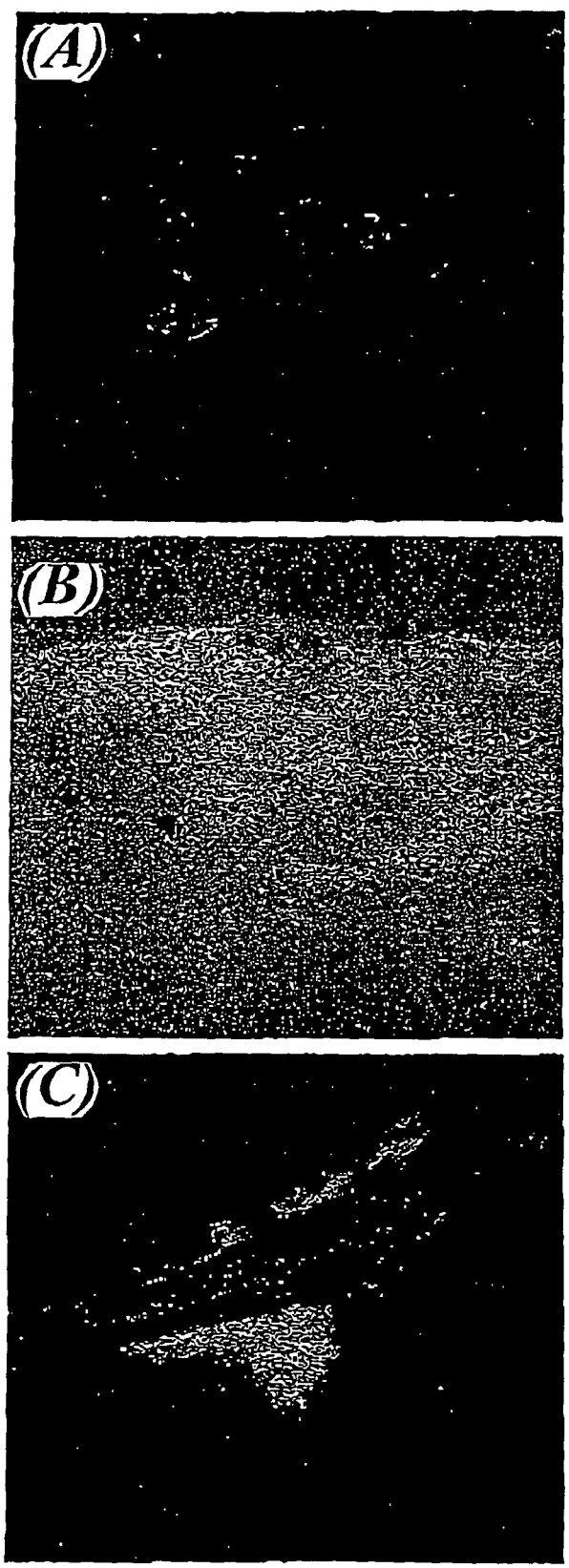

FIG. 13 A-C demonstrates the effect of TGase treatment on staining for tTGase in CT26 tumour sections (magnification ×40).

Figure 14:
Figure 14:

FIGS. 14 A and B demonstrates the effect of TGase treatment on staining for ε(γ-glutamyl) lysine cross-links in CT26 tumour sections (magnification ×10).

EXAMPLES

Example 1

Inhibition of Angiogenesis In Vitro
I—Immunohistochemical Analysis of the Effect of TGase on ECV304 Cells Materials and Methods An in vitro system of angiogenesis/tubulogenesis was developed to evaluate the efficacy of TGase administration on angiogenesis. ECV304 is an endothelial-like cell line resulting from spontaneous mutation that has recently been shown to be epithelial in origin (Brown J., et al., 2000, *Lab. Invest.* 80:37-45). This cell line exhibits several endothelial cell markers, has the propensity to spontaneously form tubular networks when cultured on Matrigel (Hughes, S. E., 1996, *Exp. Cell Res*. 225, 171-185), and has been shown to respond to novel and established angiogenic modulators in the same manner as primary human umbilical vein endothelial cells and animal models of angiogenesis (Jian, L., et al., 2000, *Nat. Med.* 6, 49-55). In the model cell system described below, ECV304 cells were co-cultured with the primary human dermal fibroblast cell line C378 (isolated from human foreskin), which provides the appropriate biochemical information to stimulate the differentiation of ECV304 to form capillary-like structures.

Cell Culture and In Vitro Angiogenesis Model

ECV304 cell lines S3 (a neomycin resistant transfected control cell line phenotypically similar to wild type cells) and B4 (a tTGase antisense transfected cell line [Jones, R. A., et al., 1997, *J. Cell Sci*. 110, 2461-2472]) and C378 were routinely cultured in Dulbecco's Modified Eagles Media (DMEM) supplemented with 2 mM glutamine and 10% (v/v) foetal calf serum (FCS). Cells were harvested by exposure to 0.25% (w/v) bovine trypsin in phosphate buffered saline (PBS) pH 7.4, and collected cells were washed in normal culture media, counted and seeded into the appropriate tissue culture vessel. Standard angiogenesis experiments were performed in 12-well cell culture plates, and 2×10⁴ ECV304 cells and 2×10⁴ C378 cells were seeded into 1 ml of normal growth media. For immunochemical staining experiment, 2×10³ cells of each cell type were seeded into 300 ml of growth medium in 8-well glass chamber slides. Co-cultures were incubated at 37° C. in a humidified atmosphere containing 5% (V/V) $CO_2$, and tubules were allowed to develop spontaneously over a 14-day period, with regular changes of growth media every 72 hours.

Treatments

For cultures treated with purified tTGase, a dose response with 1, 10 and 50 µg pig guinea pig liver transglutaminase (gplTGase) was performed with two separate dosing regimes. gplTGase was activated by pre-incubation with 10 mM DTT on ice for one hour prior to its addition to cultures. The highest amount of DTT present in the cultures was 0.5 mm for the 50 µg gplTGase treatment, and control cultures were treated with DTT accordingly. In some experiments, cultures were treated with two administrations of exogenous enzyme on day 1 and day 4 of the experiment. Further studies extended the dose regime to include five gplTGase treatments, on days 1, 4, 7, 10 and 13.

Immunohistochemistry and Fluorescence Microscopy

Cultures in 12-well plates that demonstrated mature tubule formation were fixed in 3.7% (w/v) paraformaldehyde in PBS (pH 7.4) for 15 min then permeabilised using 0.1% Triton X-100 in PBS (pH 7.4) for 10 min. Non-specific protein binding was blocked by incubating fixed cells with 300 µl of 3% (w/v) bovine serum albumin (BSA) overnight at 4° C. Blocked plates were then incubated with the primary antisera (see table 5), diluted in the above buffer, for 2 hours at 37° C. with gentle shaking. Next, plates were washed three times and incubated with the appropriate species-specific secondary antibody (see table 5) conjugated to Horseradish peroxidase (HRP) for 2 hours at 37° C. with gentle shaking. Following antibody treatment, plates were washed three times and developed with the chromogenic HRP substrate diaminobenzidine (DAB) and $H_2O_2$ with metal enhancer. The staining reaction was terminated by removal of the developer and wells were washed with PBS. Staining was observed by light microscopy and photographed using an Olympus digital camera.

TABLE 5

List of antibodies used for immunohistochemical analyses

| Antigen | Species source | Comments | Dilution | Label |
|---|---|---|---|---|
| PECAM | Mouse | Endothelial/angiogenesis marker | 1/100 | — |
| UEA-1 | Rabbit | Endothelial cell marker | 1/50 | — |
| tTGase | Mouse | — | 1/50 | — |
| Collagen I | Goat | Angiogenesis marker | 1/100 | — |
| Mouse IgG | Goat | Secondary antibody | 1/200 | HRP |
| Goat IgG | Rabbit | Secondary antibody | 1/200 | HRP |
| Rabbit IgG | Goat | Secondary antibody | 1/200 | HRP |

For visualisation of tTGase activity in situ, cells were cultured in 8-well chamber slides in growth medium containing 0.5 mM fluorescein cadaverine, from day 7 to 14 of the experiment. This time-period corresponds to the tubular development period in culture that occurs after the co-culture becomes a uniform monolayer of cells. Cultures that demonstrated mature tubule formation were fixed and permeabilised with two washes of methanol at −20° C. for 20 min. Stained cultures were mounted in 70% (v/v) glycerol and viewed using a Leica TCSNT confocal microscope.

Results and Conclusions

Using the in vitro model of angiogenesis/microtubule formation described above, it was possible to assess the effect of transglutaminase treatment on tubule formation in ECV304 cells.

Effect of Repeated (×5) Administration of TGase on Angiogenesis

Cell cultures were treated with 1, 10 or 50 µg/ml of guinea pig liver transglutaminase (gplTGase) on days 1, 4, 7, 10 and 13 of culture.

Repeated administration of the exogenous TGase to the culture medium was necessary since transglutaminase either becomes degraded by matrix metalloproteinases or crosslinks itself into the matrix, thereby becoming inactive.

Figure 1:
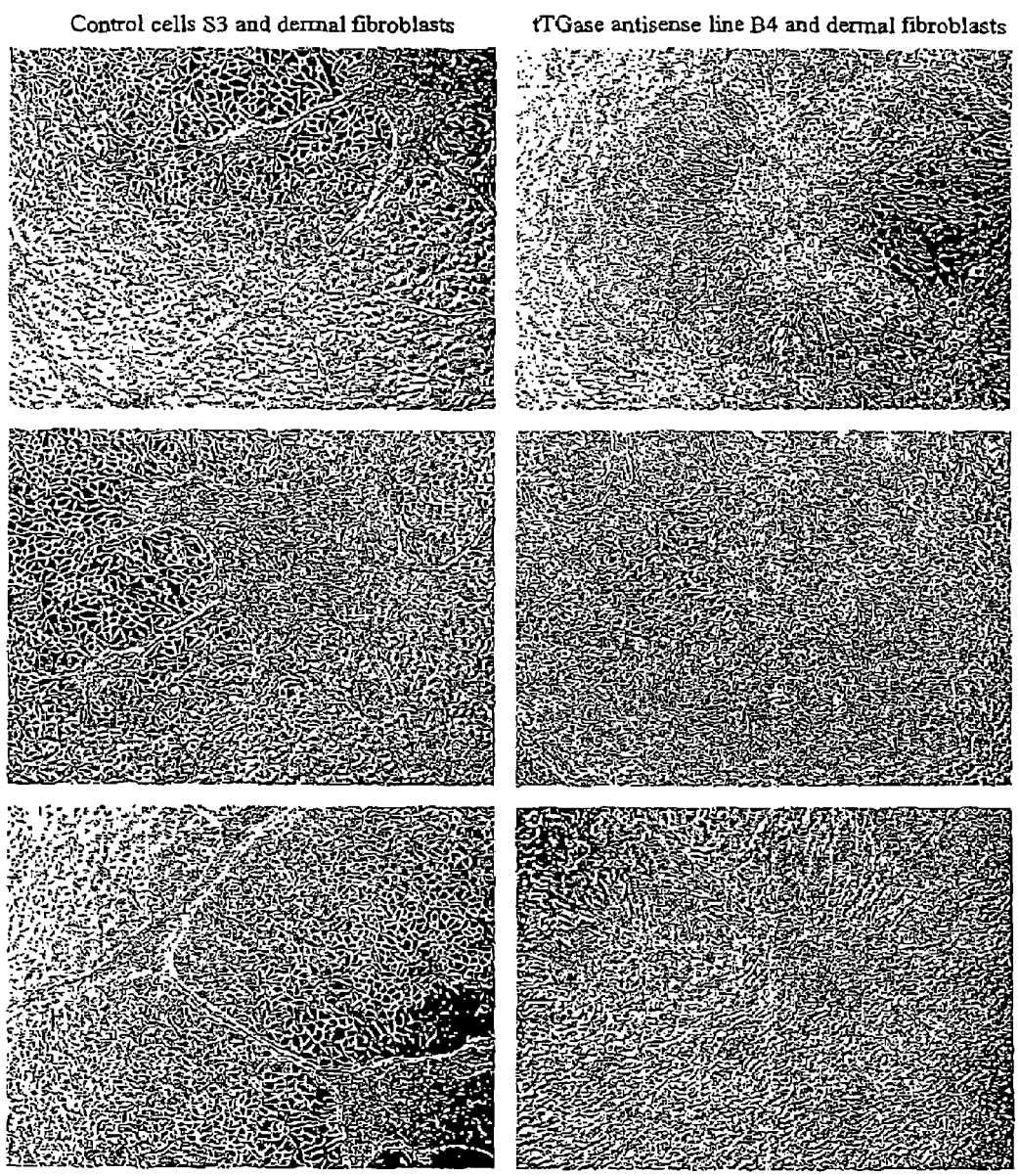
FIG. 1 demonstrates delayed angiogenesis in tTGase deficient cell line B4 compared to control cell line S3. Illustrations show living cells on 10th day in culture.
Figure 2:
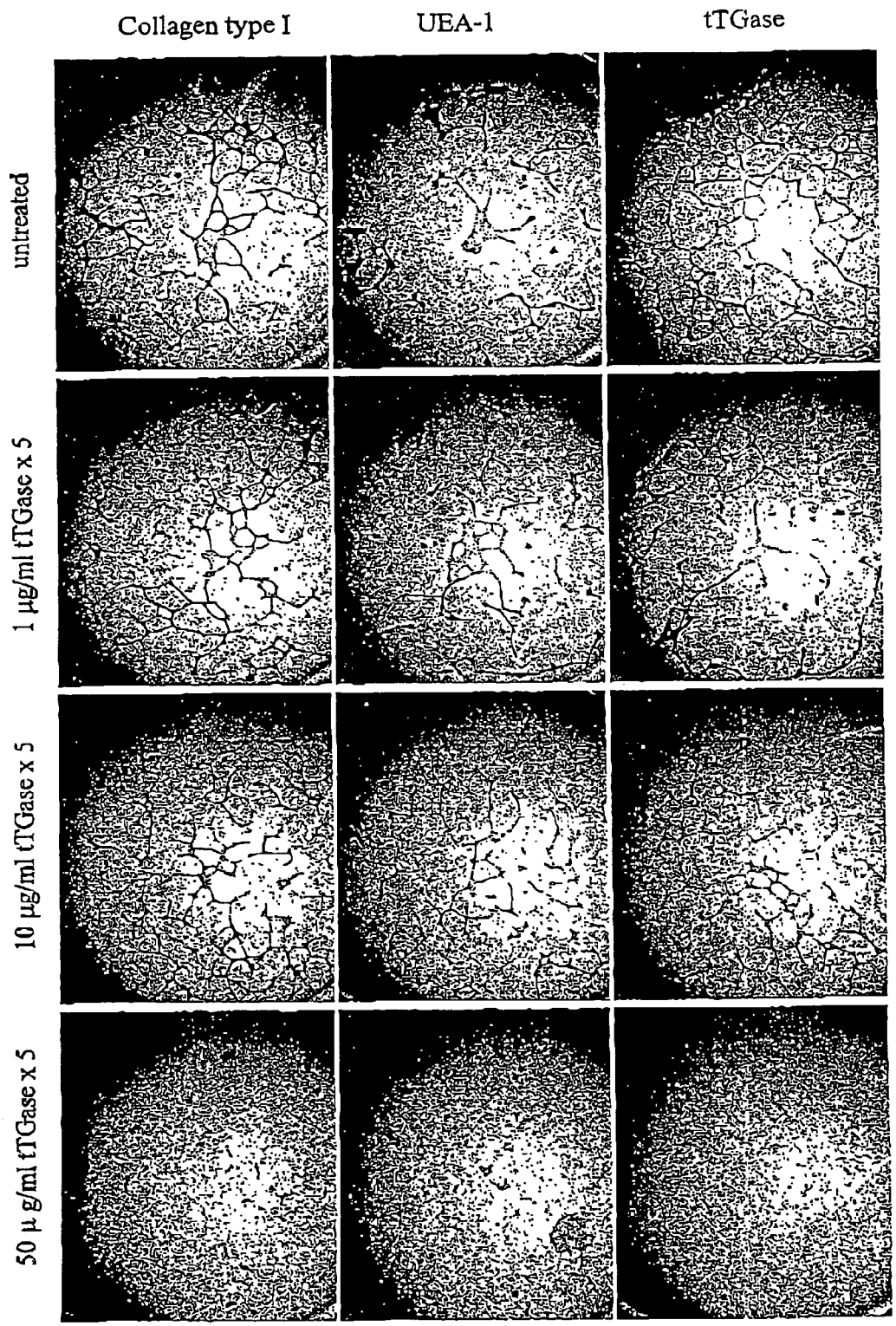
FIG. 2 demonstrates inhibition of angiogenesis through five administrations of 1, 10 or 50 µg of active gplTGase. Tubules were visualised by staining for collagen type I, UEA-1 and tTGase, as indicated.

Microtubule formation was then visualised on Day 14 by staining the cells for either collagen type I, UEA-1 or tTGase (see FIG. 2).

Effect of Repeated (×5) Administration of TGase on Angiogenesis

At doses of 1 and 10 µg/ml, five treatments with tissue transglutaminase did not appear to have significant effect on microtubule formation in cultured ECV304 cells. Thus, staining for collagen type I, UEA-1 or tTGase was not noticeably different from that in untreated cells. Microtubule formation was clearly visible in all cases.

In contrast, five treatments with tissue transglutaminase at a dose of 50 µg/ml resulted in a significantly reduction in staining for collagen type I, UEA-1 and tTGase compared to staining in untreated (control) cells. Microtubule formation was almost completely inhibited.

Effect of (2×) Administration of Tgase on Angiogenesis

Figure 3:
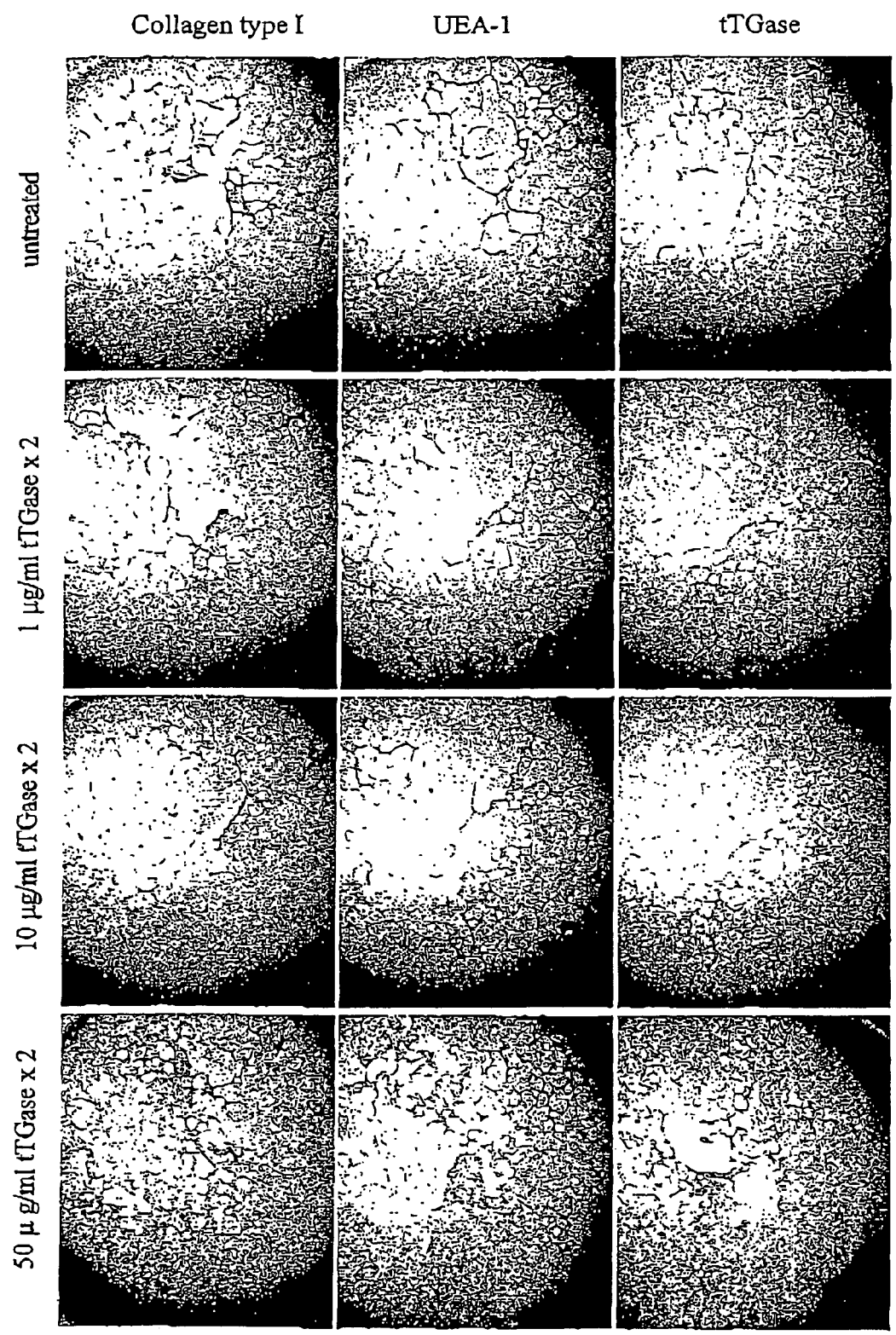
FIG. 3 demonstrates stimulation of angiogenesis through two administrations of 1, 10 or 50 µg of active gplTGase. Tubules were visualised by staining for collagen type I, UEA-1 and tTGase, as indicated.

Cell cultures were treated with 1, 10 or 50 µg/ml of guinea pig liver transglutaminase (gplTGase) on days 1 and 4 of culture. Microtubule formation was then visualised by staining the cells for either collagen type I, UEA-1 or tTGase (see FIG. 3).

At doses of 1 and 10 µg/ml, two treatments with tissue transglutaminase did not appear to have significant effect on microtubule formation in cultured ECV304 cells. Thus, staining for collagen type I, UEA-1 or tTGase was not noticeably different from that in untreated cells. Microtubule formation was clearly visible in all cases.

At a dose 50 µg/ml, two treatments with tissue transglutaminase staining for collagen type I, UEA-1 or tTGase was significantly enhanced compared to staining in untreated (control) cells. Increased microtubule formation was evident from each of the stains.

Effect of Suramin Administration on Angiogenesis

Figure 4:
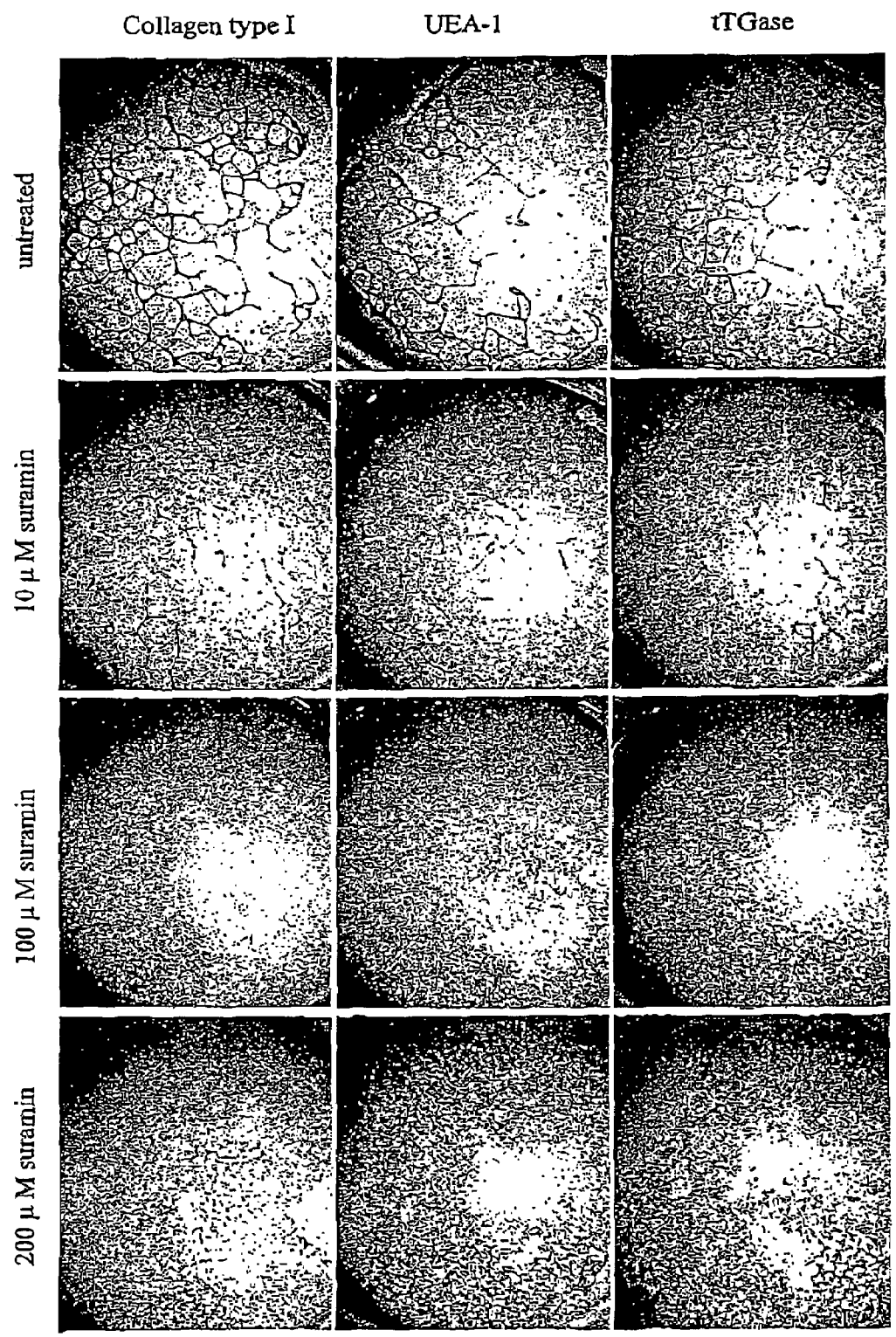
FIG. 4 demonstrates inhibition of angiogenesis through administration of standard angiogenesis inhibitor suramin. Tubules were visualised by staining for collagen type I, UEA-I and tTGase, as indicated.

As a positive control, cultured ECV304 cells were incubated in various concentrations of the known angiogenesis inhibitor, suramin (see Gagliardi et al, 1992, Cancer Res. 52(18):5073-5). At the lowest dose of 10 µM suramin, microtubule formation (as visualised by collagen type I, UEA-1 and tTGase staining) was significantly reduced compared to that observed in untreated cells. At doses of 100 µM and 200 µM, microtubule formation was completely eradicated (see FIG. 4).

Conclusions

The data demonstrate that continued administration (e.g. five times) of transglutaminase can result in a significant inhibition of angiogenesis, whereas initial administrations (e.g. two times) of tTGase lead to an increase in angiogenesis.

Example 2

Inhibition of Angiogenesis In Vitro
II—Immunohistochemical Analysis of the Effect of TGase Using a Commercially Available Angiogenesis Assay Kit Materials and Methods The inhibition of angiogenesis following transglutaminase administration was further demonstrated using a commercially available angiogenesis assay kit (Catalogue No ZHA-1000, TCS Biologicals Ltd, Botolph Claydon, Buckinghamshire, UK).

The kit is supplied as a growing culture of human endothelial cells (together with support cells) in a 24-well plate.

Angiogenesis was measured using the mnanufacturer's protocol (supplied with the kit).

In brief, on receipt of the kit from the supplier (day 1) 0.5 ml of fresh media (as supplied with the kit) was added to each well of the plate and the cells were cultured in 5% $CO_2$ (v/v) in a humidified atmosphere at 37° C. Culture media was replaced with fresh stock on days 4, 7 and 9. On day 11, the culture media was removed and cells were fixed by the addition of 1 ml/well 70% (v/v) ethanol. The cells were then stained using a rabbit anti-human von Willebrand factor and revealed using an anti-rabbit HRP conjugate and DAB substrate, as described in Example 1.

Three treatment groups were used in the experiment as follows:

| | |
|---|---|
| Group A | Untreated (control) |
| Group B | 2 × 25 µg guinea pig liver transglutaminase (25 µg TGase/0.5 ml media was added on days 1 and 4 of culture) |
| Group C | 4 × 25 µg guinea pig liver transglutaminase (25 µg TGase/0.5 ml media was added on days 1, 4, 7 and 9 of culture) |

Results

Figure 5:
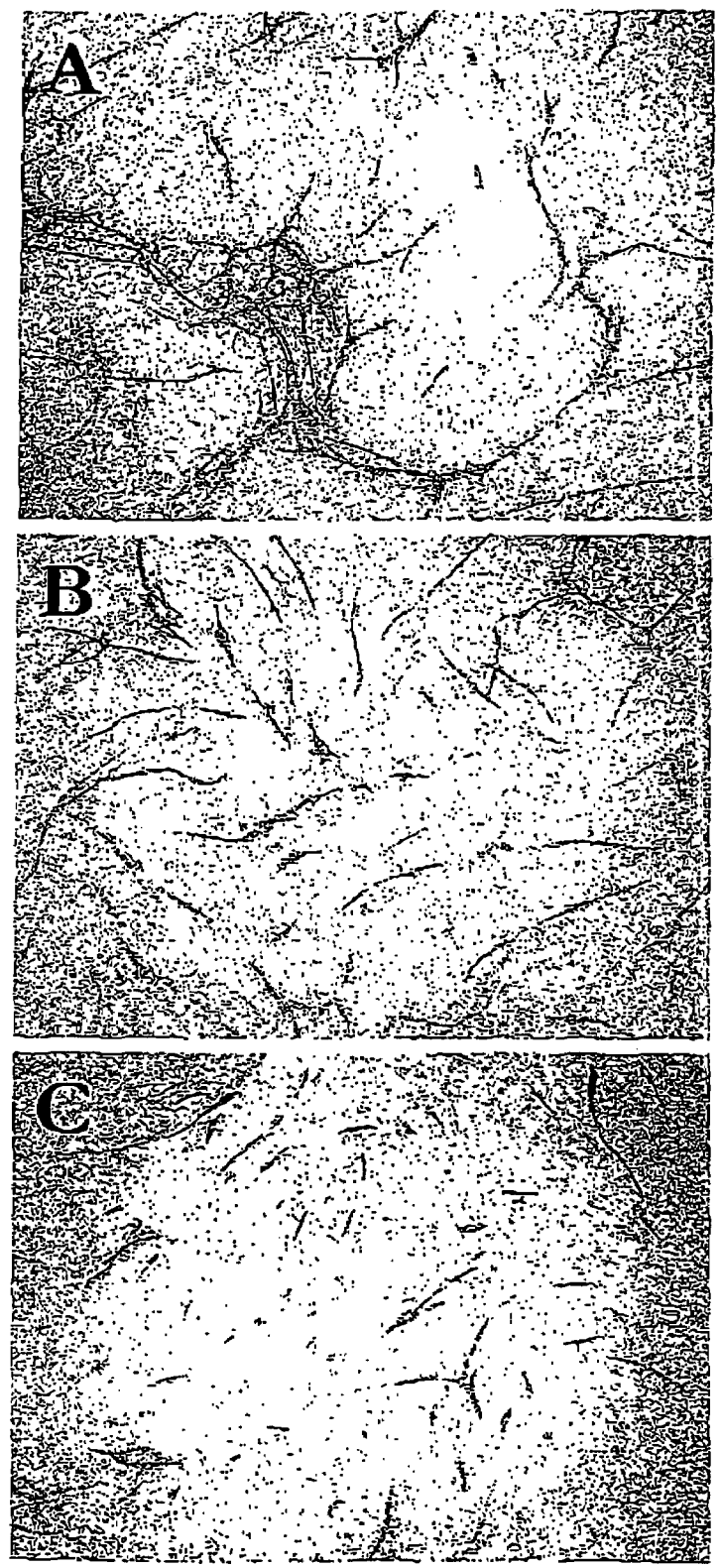
FIG. 5 demonstrates inhibition of angiogenesis, compared to (A) untreated controls, following (B) two or (C) four administrations of 25 μg of active gplTGase Tubules were visualised using a commercial angiogenesis kit obtained from TCS Biologicals Ltd.

FIG. 5 shows the effect of TGase administration on angiogenesis, as measured using the TCS angiogenesis assay kit.

Extensive microtubule formation is observed in the untreated control cell culture (A), which is progressively reduced by treatment with increasing doses of TGase (B and C).

Example 3

Inhibition of Angiogenesis In Vitro III—Western Blot Analysis of the Effect of TGase on Levels of TGase, Fibronectin and Cross-Link Staining Materials and Methods Cells (TCS angiogenesis assay kit) were cultured as described in Examples 1 and 2, and then allocated to one of the following four treatment groups:

(1) Untreated controls;

(2) One dose of 25 µg gplTGase, administered on day 2 after receipt of the kit (cultures are started by the manufacture prior to shipping the kit);

(3) Two doses of 25 µg gplTGase, administered on days 2 and 5;

(4) Four doses of 25 µg gplTGase, adminstered on days 2, 5, 8 and 10.

Each treatment group (i.e. well) comprises approximately $0.5 \times 10^6$ cells on day 1 and approximately $2 \times 10^6$ cells on day 11.

On day 11, cells were washed three times in phosphate buffered saline (PBS) pH7.4 and directly solubilised in 150 µl of 2×SDS-PAGE Laemmli sample buffer (Product Code S3401 Sigma)

Samples were boiled for five minutes and then 10 µl loaded into a well on an 8% (w/v) polyacrylamide gel. Electrophoresis was performed for two hours at 150 V, following which the gels were electroblotted onto nitrocellulose membranes for three hours at 90 mA per gel.

The blotted membranes were washed and blocked in TBS-T pH7.4 (20 mM Tris-HCl: 150 mM NaCl: 0.05% (v/v) Tween 20) containing 5% (w/v) dried milk powder (e.g., Marvel®) for two hours at room temperature, and then incubated overnight at 4° C. with one of the following primary antibodies:

(a) Mouse monoclonal anti-tTGase antibody (Cub7402, Neo-Markers, Stratech, Luton, UK), diluted 1 in 1000 in TBS-T pH7.4;

(b) Rabbit polyclonal anti-fibronectin antibody (Product Code F3648, Sigma), diluted 1 in 3000 in TBS-T pH7.4; or (c) Mouse monoclonal anti-ϵ(γ-glutamyl) lysine antibody (81D4, Abcam, Cambridge, UK), diluted 1 in 300 in TBS-T pH7.4.

The following day, membranes were washed three times in TBS-T pH7.4, then incubated for two hours at room temperature in blocking buffer (TBS-T pH7.4 containing 5% (w/v) dried milk powder) containing one of the following secondary antibodies fused to horse radish peroxidase (HRP), as appropriate:

(a) Anti-mouse IgG antibody-HRP (Product Code P0447, DAKO), diluted 1 in 1000; or (b) Anti-rabbit IgG antibody-HRP (Product Code A0545, Sigma), diluted 1 in 3000.

Following this incubation, the membranes were washed three times in TBS-T pH7.4 and then twice in PBS pH 7.4, before staining was revealed using enhanced chemiluminescence (Xu H J et al, 1992, *J. Immunol. Methods* 146:241-247).

Results tGase Staining

Figure 6:
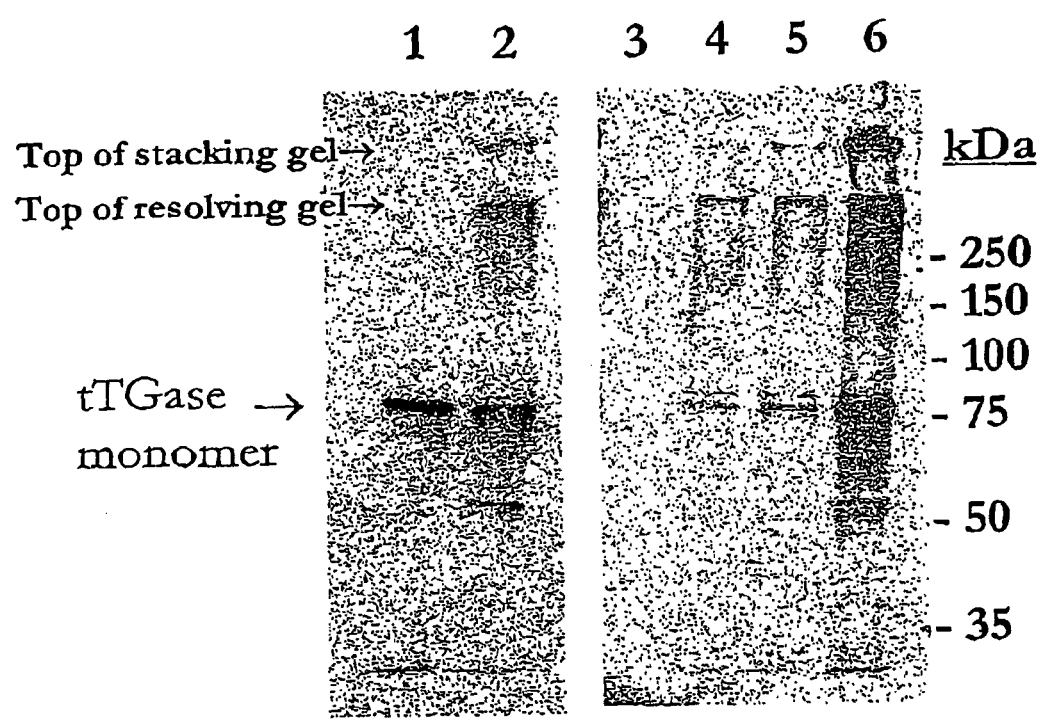
FIG. 6 demonstrates the polymerisation of TGase following treatment of angiogenesis cell cultures with TGase, observed by western blotting, In control experiments, 4 μg gplTGase was preincubated for one hour at 37° C. with either 2 mM DTT/5 mM EDTA (lane 1) or 2 mM DTT/2 mM $Ca^{2+}$ (lane 2), then solubilised in 20 μl 2×SDS-PAGE sample buffer and loaded on to the 8% polyacrylamide gel. Angiogenesis cultures were either untreated (lane 3), treated with one dose of 25 μg gplTGase, administered on day 2 (lane 4), treated with two doses of 25 μg gplTGase, administered on days 2 and 5 (lane 5), or treated with four doses of 25 μg gplTGase, administered on days 2, 5, 8 and 10 (lane 6). On day 11, cultures were solubilised in 150 μl 2×SDS-PAGE sample buffer and 10 μl was then loaded on to the 8% polyacrylamide gel. Following electrophoresis, nitrocellulose blots were taken and immunoprobed with anti-tTGAse monoclonal antibody, which was revealed using an anti-mouse IgG-HRP conjugate by enhanced chemiluminescence.

The effect of TGase-treatment on TGase staining is shown in FIG. 6.

In untreated control cells (lane 3), no TGase staining was observed. However, it is apparent from lanes 3 to 6 that increasing doses of TGase resulted in significant TGase staining, with evidence of extensive polymerisation of the TGase.

Fibronectin Staining

Figure 7:
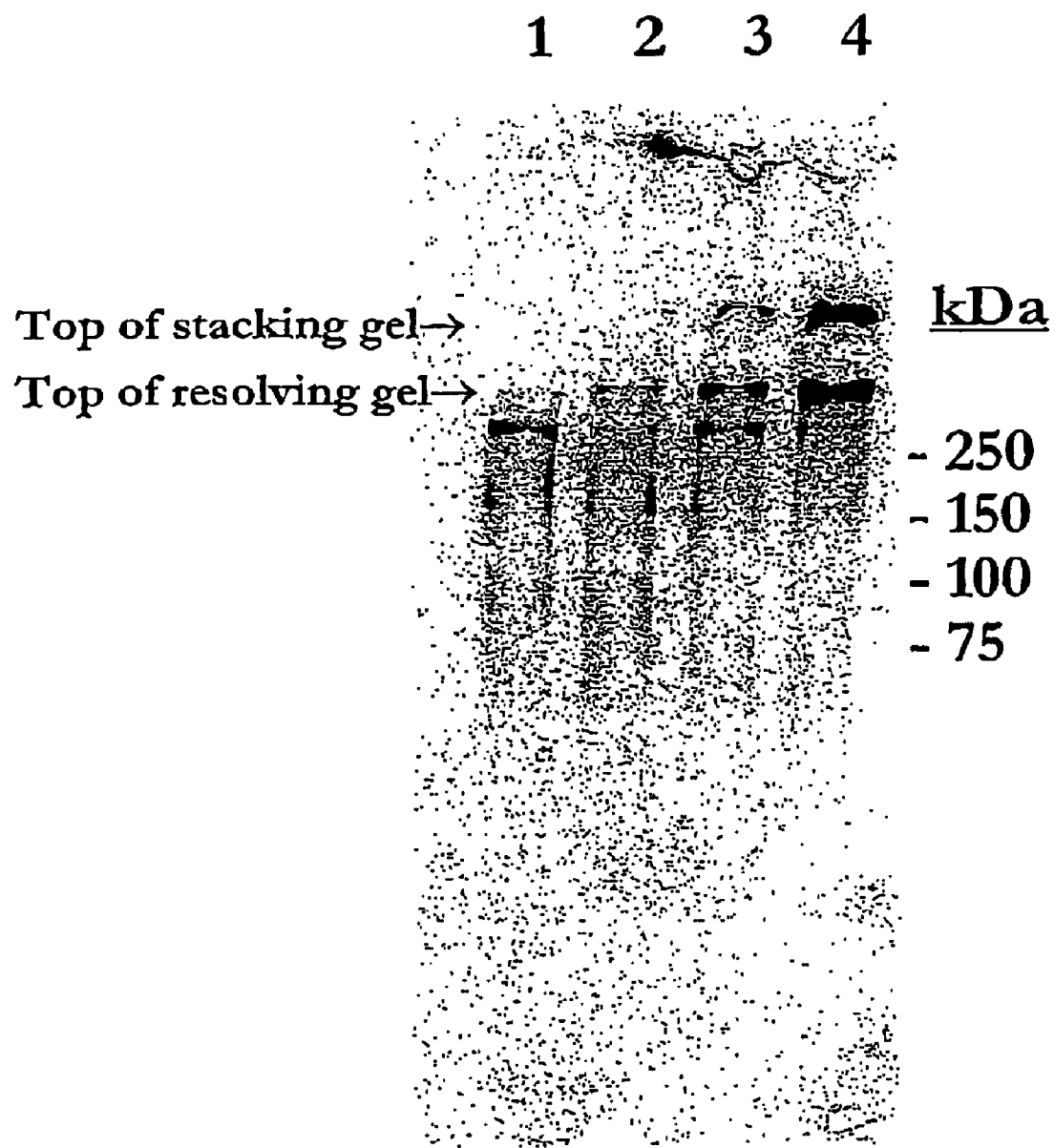
FIG. 7 demonstrates the polymerisation of fibronectin following treatment of angiogenesis cell cultures with TGase, observed by western blotting. Angiogenesis cultures were either untreated (lane 1), treated with one dose of 25 μg gplTGase, administered on day 2 (lane 2), treated with two doses of 25 μg gplTGase, administered on days 2 and 5 (lane 3), or treated with four doses of 25 μg gplTGase, administered on days 2, 5, 8 and 10 (lane 4). On day 11, cultures were solubilised in 150 μl 2×SDS-PAGE sample buffer and 5 μl was then loaded on to the 8% polyacrylamide gel. Following electrophoresis, nitrocellulose blots were taken and immunoprobed with anti-fibronectin rabbit polyclonal antibody, which was revealed using an anti-rabbit IgG-HRP conjugate by enhanced chemiluminescence.

The effect of TGase-treatment on fibronectin staining is shown in FIG. 7.

In untreated control cells (lane 1), little or no polymerisation of fibronectin was observed. However, it is apparent from lanes 2 to 4 that increasing doses of TGase resulted in extensive polymerisation of the fibronectin, resulting in increased staining of high molecular weight bands.

ϵ(γ-glutamyl) Lysine Staining

Figure 8:
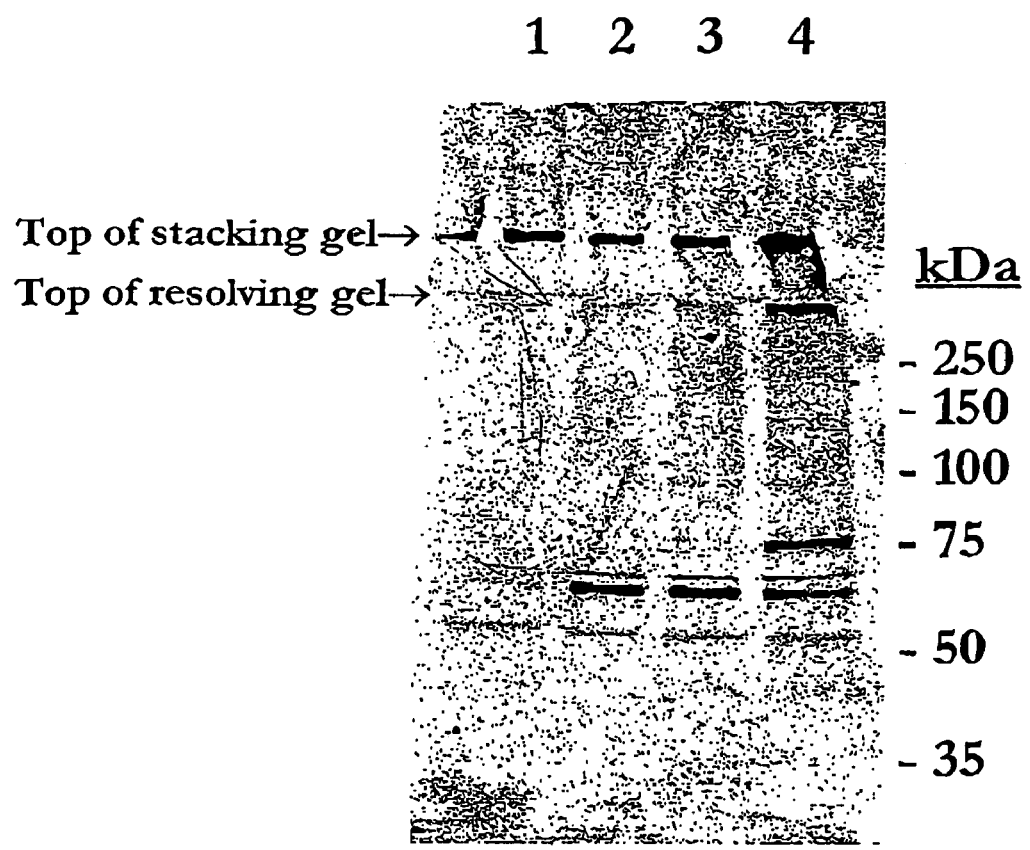
FIG. 8 demonstrates the increase in ε(γ-glutamyl) lysine cross-links following treatment of angiogenesis cell cultures with TGase, observed by western blotting. Angiogenesis cultures were either untreated (lane 1), treated with one dose of 25 μg gplTGase, administered on day 2 (lane 2), treated with two doses of 25 μg gplTGase, administered on days 2 and 5 (lane 3), or treated with four doses of 25 μg gplTGase, administered on days 2, 5, 8 and 10 (lane 4). On day 11, cultures were solubilised in 150 μl 2×SDS-PAGE sample buffer and 30 μl was then loaded on to the 8% polyacrylamide gel. Following electrophoresis, nitrocellulose blots were taken and immunoprobed with anti-ε(γ-glutamyl) lysine monoclonal antibody, which was revealed using an anti-mouse IgG-HRP conjugate by enhanced chemiluminescence.

The effect of TGase-treatment on ϵ(γ-glutamyl) lysine staining is shown in FIG. 8.

In untreated control cells (lane 1), low levels of ϵ(γ-glutamyl) lysine staining were observed. However, it is apparent from lanes 2 to 4 that increasing doses of TGase resulted in significant ϵ(γ-glutamyl) lysine staining, with evidence of extensive polymerisation of proteins.

Conclusion

The western blots demonstrate that TGase treatment causes cross-linking of proteins (including TGase itself into high molecular weight polymers which are able to enter, but cannot traverse, the 8% polyacrylamide resolving gel.

Indeed, some very high molecular weight polymers are observed which are able to enter, but cannot traverse, the 4% polyacrylamide stacking gel Example 4

Inhibition of Angiogenesis In Vivo—Effect of TGase Treatment on CT26 Tumour Growth in Mice Materials and Methods CT26 Tumour Model Female Balb/c mice (six to eight week old, Harlan Olac, Bicester, UK) were implanted with $1 \times 10^5$ CT26 tumour cells in 0.1 ml phosphate buffered saline (PBS) pH7.4 by subcutaneous injection in the right flank. Nine days later, when the tumours had reached approx. 17 $mm^2$ in size, animals were randomly divided into two groups of ten animals.

The first treatment group received intra-tumour injections of 50 μl guinea pig liver TGase (4 mg/ml) (Sigma, Poole, UK) in Dulbecco's PBS pH 7.4 (without calcium and magnesium chloride), supplemented with 2 mM $CaCl_2$ and 2 mM dithiothreitol (DTT) on days 9, 11, 14, 16 and 18. The second treatment group received parallel injection of PBS with $CaCl_2$ and DTT but without the TGase.

Subcutaneous tumour growth was measured at 3 to 6 day intervals with a calliper, and animals were sacrificed when any individual tumour size exceeded 100 $mm^2$. (N.B. Some animals developed more than one tumour. In such animals, tumour size was calculated as the sum of the total tumours in the animal).

Immunohistochemical Analysis

Tumour specimens were taken from the mice, frozen in liquid nitrogen were embedded in OCT (Product Code 36060-4B, BDH). Sections (10 μm) were then cut using a cryostat, air-dried and then fixed in ice-cold acetone for 15 minutes, before being blocked with 3% (w/v) bovine serum albumin in PBS pH7.4 overnight at 4° C.

The sections were then incubated at 37° C. for two hours with one of the following primary antibodies:
(a) Mouse anti-tTGase antibody, diluted 1 in 20 (Cub7402, NeoMarkers, Stratech, Luton, UK);
(b) Mouse anti-ϵ(γ-glutamyl) lysine antibody, diluted 1 in 20 (81D1C2, Abcam Cambridge, UK);
(c) Goat anti-von Willebrand factor antibody, diluted 1 in 20 (C-20, Santa Cruz, Autogen, Bioclear, Wiltshire, UK);
(d) Goat anti-collagen type I antibody, diluted 1 in 50, (Product No. AB758, Chemicon, Harrow, UK); or
(e) Mouse anti-collagen type III antibody, diluted 1 in 50, (FH-7A, Sigma, Dorset, UK).

Staining was revealed by incubation for 2 hours at 37° C. with either an anti-mouse IgG-TRITC conjugate (Product Code AP192R, Chemicon, Harrow, UK), diluted 1 in 50, or an anti-goat IgG-TRITC conjugate, diluted 1 in 50 (Product Code AP180R, Chemicon, Harrow, UK). Negative controls for staining were obtained by omission of the primary antibody and stained sections were mounted in 70% (v/v) glycerol and viewed on a confocal microscope (TCSNT, Leica).

Results

Tumour Size

Figure 9A:
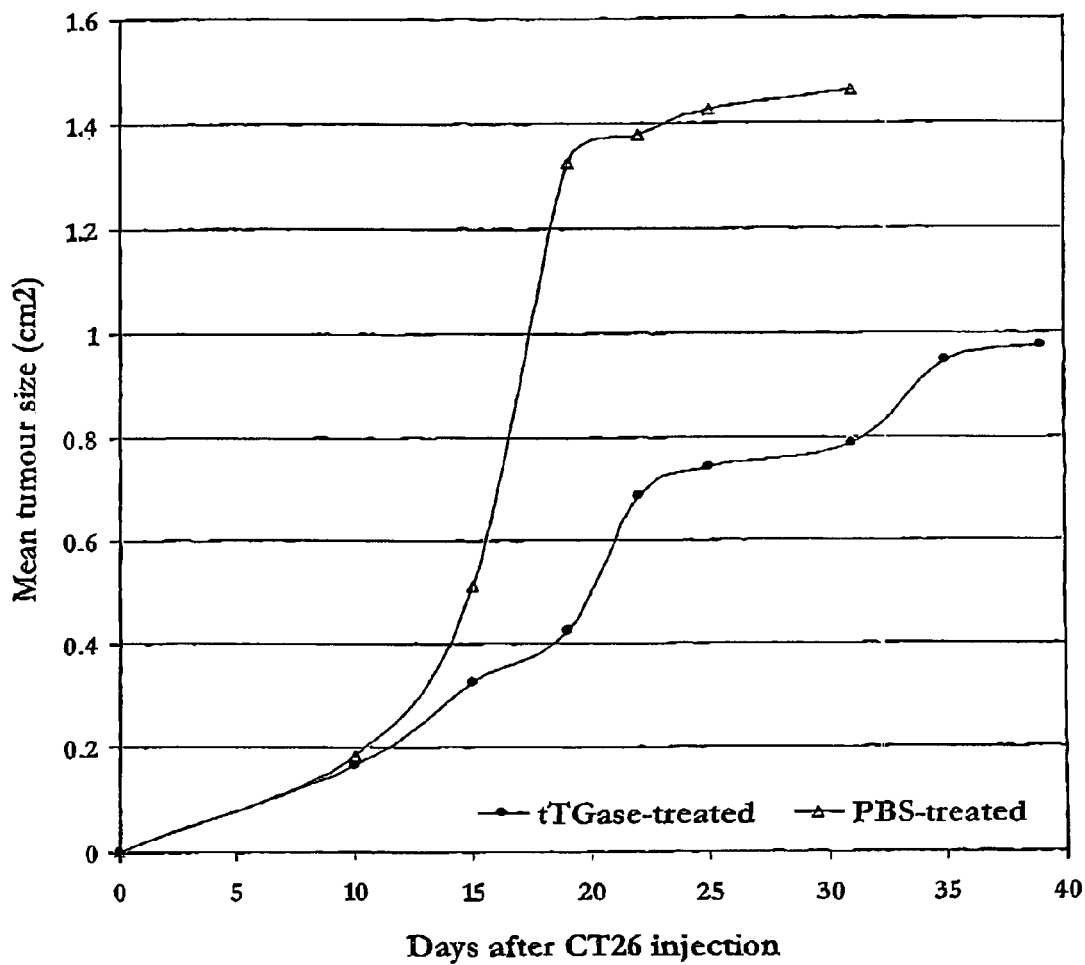
FIG. 9 demonstrates the effect of TGase treatment (on days 9, 11, 14, 16 and 18 after surgical implantation of tumour cells) on mean tumour size in the CT26 tumour model in mice.
Figure 9B:
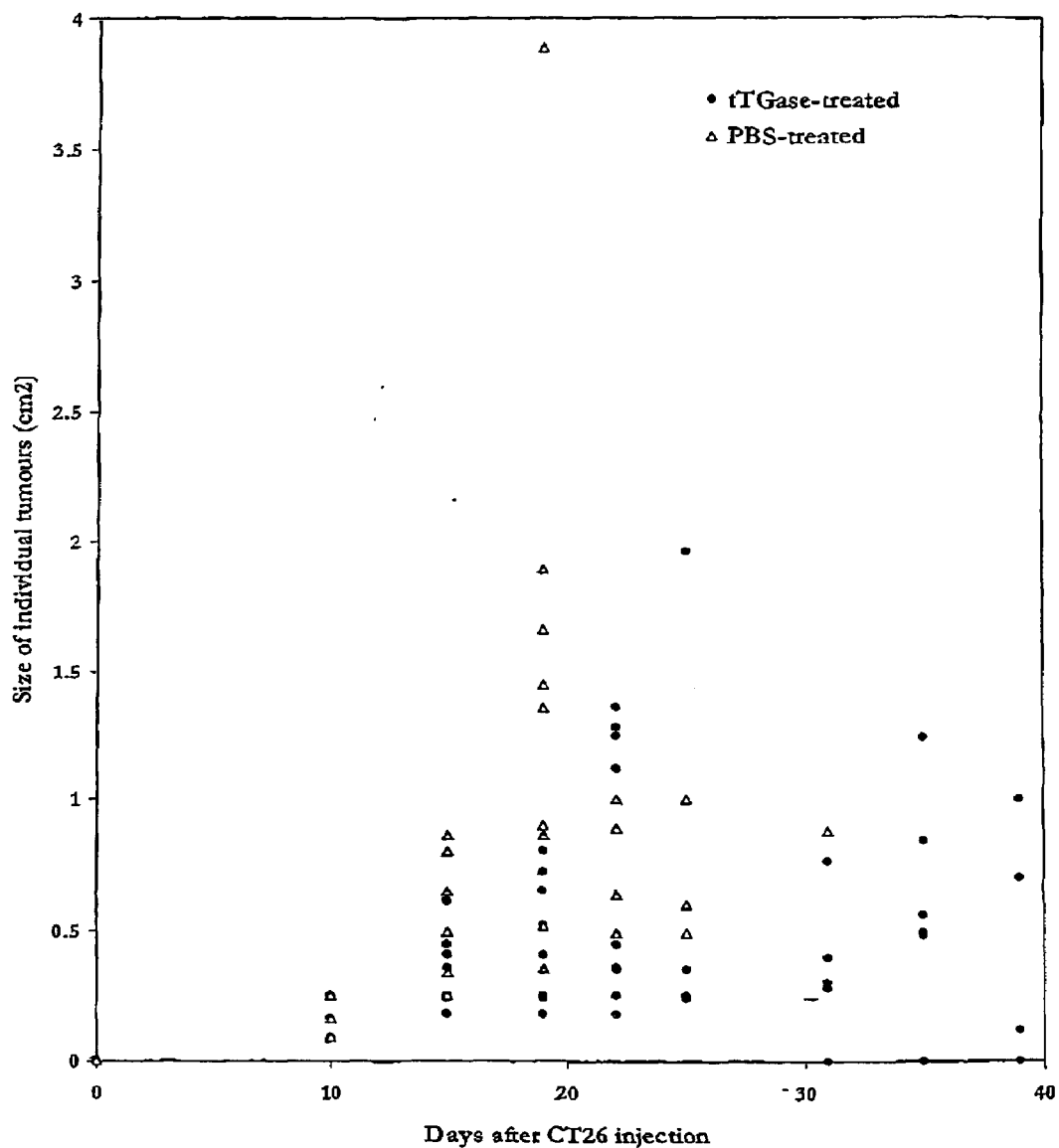

The effect of TGase treatment on mean size of the CT26 tumour is shown in FIG. 9.

TGase treatment was found to result in a significant attenuation of tumour growth. In some TGase-treated animals, the tumour was observed to regress (data not shown.

Von Willebrand Factor Staining

Staining for von Willebrand factor (an endothelial cell marker) is shown in FIG. 10.

In the PBS-treated tumour (A), von Willebrand factor staining is seen in ring-like structures indicating the presence of new blood vessels in the body of the tumour. In contrast, in the tTGase-treated regressing tumour, staining is largely absent (B). Where von Willebrand factor staining is detected in the tTGase-treated tumour, organised blood vessels are not observed, suggesting that tTGase-treatment has interfered with angiogenesis.

Collagen Type I Staining

Staining for collagen type I (a fibrosis marker) is shown in FIG. 11.

For the PBS-treated tumour (A), collagen I is diffusely distributed in the tumour body but found more concentrated at the edge. In contrast in the regressing tumour (B), what appears to be dense collagen I staining is found in structures spread throughout the tumour (see arrows), indicating that a fibrotic-like matrix has formed.

Collagen Type III Staining

Staining for collagen type III (which is known to be particularly rich in endothelial cell basement membranes) is shown in FIG. 12.

For PBS-treated growing tumours (A), collagen III staining is sparse in the body of the tumour and is mainly seen in blood vessel structures (see arrow). In contrast, in the tTGase-treated regressing tumour (B) staining is more random and not found in blood vessel structures, which appear to be largely absent. Collagen III staining appears present in dense matrix structures within the regressing tumour (see arrows).

tTGase Staining

Staining for tTGase is shown in FIG. 13.

In the PBS-treated tumour (A), tTGase staining is very weak and diffuse in the body of the tumour and is confined to the endothelial cells of the new blood-vessels (arrows), which are densely distributed in these control tumours. In contrast, in the tTGase-treated tumour (B and C) there is no evidence of organised staining of tTGase in endothelial cells found in new blood vessels, providing further evidence for inhibition of an angiogenesis. The staining appears to be matrix-associated in concentrated areas, reflecting the injection of the enzyme into the tumour and indicating its presence remains in the tumour during regression.

ϵ(γ-glutamyl) Lysine Staining

Staining for ϵ(γ-glutamyl) lysine is shown in FIG. 14.

The PBS-treated tumour (A) contains little crosslinking when analysed by immunohistochemistry. In contrast, dense matrix-like staining is observed in the regressing tumour (B)

providing evidence that the injected enzyme bas lead to increased protein cross-linking.

Example 5

Exemplary Pharmaceutical Formulations

The following examples illustrate pharmaceutical formulations according to the invention in which the active ingredient is a transglutaminase.

Example A

Tablet

| Active ingredient | 100 mg |
|---|---|
| Lactose | 200 mg |
| Starch | 50 mg |
| Polyvinylpyrrolidone | 5 mg |
| Magnesium stearate | 4 mg |
| | 359 mg |

Tablets are prepared from the foregoing ingredients by wet granulation followed by compression.

Example B

Ophthalmic Solution

| Active ingredient | 0.5 g |
|---|---|
| Sodium chloride, analytical grade | 0.9 g |
| Thiomersal | 0.001 g |
| Purified water to | 100 ml |
| pH adjusted to | 7.5 |

Example C

Tablet Formulations

The following formulations A and B are prepared by wet granulation of the ingredients with a solution of povidone, followed by addition of magnesium stearate and compression.

| | mg/tablet | mg/tablet |
|---|---|---|
| Formulation 1 | | |
| Active ingredient | 250 | 250 |
| Lactose B.P. | 210 | 26 |
| Povidone B.P. | 15 | 9 |
| Sodium Starch Glycolate | 20 | 12 |
| Magnesium Stearate | 5 | 3 |
| | 500 | 300 |
| Formulation 2 | | |
| Active ingredient | 250 | 250 |
| Lactose | 150 | — |
| Avicel PH 101 ® | 60 | 26 |
| Povidone B.P. | 15 | 9 |
| Sodium Starch Glycolate | 20 | 12 |
| Magnesium Stearate | 5 | 3 |
| | 500 | 300 |
| Formulation 3 | | |
| Active ingredient | 100 | |
| Lactose | 200 | |
| Starch | 50 | |
| Povidone | 5 | |
| Magnesium stearate | 4 | |
| | 359 | |

The following formulations, D and A, are prepared by direct compression of the admixed ingredients. The lactose used in formulation E is of the direction compression type.

| | mg/capsule |
|---|---|
| Formulation 4 | |
| Active Ingredient | 250 |
| Pre-gelatinised Starch NF15 | 150 |
| | 400 |
| Formulation 5 | |
| Active Ingredient | 250 |
| Lactose | 150 |
| Avicel ® | 100 |
| | 500 |

Formulation 6 (Controlled Release Formulation)

The formulation is prepared by wet granulation of the ingredients (below) with a solution of povidone followed by the addition of magnesium stearate and compression.

| | mg/tablet |
|---|---|
| Active Ingredient | 500 |
| Hydroxypropylmethylcellulose (Methocel K4M Premium) ® | 112 |
| Lactose B.P. | 53 |
| Povidone B.P.C. | 28 |
| Magnesium Stearate | 7 |
| | 700 |

Drug release takes place over a period of about 6-8 hours and was complete after 12 hours.

Example D

Capsule Formulations

Formulation 1

A capsule formulation is prepared by admixing the ingredients of Formulation D in Example C above and filling into a two-part hard gelatin capsule. Formulation B (infra) is prepared in a similar manner.

| Formulation 2 | mg/capsule |
|---|---|
| (a) Active ingredient | 250 |
| (b) Lactose B.P. | 143 |
| (c) Sodium Starch Glycolate | 25 |
| (d) Magnesium Stearate | 2 |
| | 420 |

| Formulation 3 | |
|---|---|
| (a) Active ingredient | 250 |
| (b) Macrogol 4000 BP | 350 |
| | 600 |

Capsules are prepared by melting the Macrogol 4000 BP, dispersing the active ingredient in the melt and filing the melt into a two-part hard gelatin capsule.

| Formulation 4 | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation 5 (Controlled Release Capsule)

The following controlled release capsule formulation is prepared by extruding ingredients a, b, and c using an extruder, followed by spheronisation of the extrudate and drying. The dried pellets are then coated with release-controlling membrane (d) and filled into a two-piece, hard gelatin capsule.

| | mg/capsule |
|---|---|
| (a) Active ingredient | 250 |
| (b) Microcrystalline Cellulose | 125 |
| (c) Lactose BP | 125 |
| (d) Ethyl Cellulose | 13 |
| | 513 |

Example E

Injectable Formulation

| | |
|---|---|
| Active ingredient | 0.200 g |

Sterile, pyrogen free phosphate buffer (pH7.0) to 10 ml

The active ingredient is dissolved in most of the phosphate buffer (35-40° C.), then made up to volume and filtered through a sterile micropore filter into a sterile 10 ml amber glass vial (type 1) and sealed with sterile closures and overseals.

Example F

Intramuscular Injection

| | |
|---|---|
| Active ingredient | 0.20 g |
| Benzyl Alcohol | 0.10 g |
| Glucofurol 75 ® | 1.45 g |

Water for Injection q.s. to 3.00 ml

The active ingredient is dissolved in the glycofurol. The benzyl alcohol is then added and dissolved, and water added to 3 ml. The mixture is then filtered through a sterile micropore filter and sealed in sterile 3 ml glass vials (type 1).

Example G

Syrup Suspension

| | |
|---|---|
| Active ingredient | 0.2500 g |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The active ingredient is added and dispersed. In the glycerol is dispersed the thickener (dispersible cellulose). The two dispersions are mixed and made up to the required volume with the purified water. Further thickening is achieved as required by extra shearing of the suspension.

Example H

Suppository

| | mg/suppository |
|---|---|
| Active ingredient (63 µm)* | 250 |
| Hard Fat, BP (Witepsol H15 - Dynamit Nobel) | 1770 |
| | 2020 |

*The active ingredient is used as a powder wherein at least 90% of the particles are of 63 µm diameter or less.

One fifth of the Witepsol H15 is melted in a steam-jacketed pan at 45° C. maximum. The active ingredient is sifted through a 200 µm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 µm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example I

Pessaries

|  | mg/pessary |
| --- | --- |
| Active ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

Example J

Microsphere Formulations

TGase may also be delivered using microsphere formulations, such as those described in Cleland (1997), *Pharm. Biotechnol.* 10:143, Lee (2001) *Curr. Opin. Biotechnol.* 11:81-84, Cleland et al. (2001) *J. Control. Release* 72:13-24 and Takeuchi et al. (2001) *Adv. Drug. Delic. Rev.* 47:39-54.

The invention claimed is:

1. A method for treating cancer in a human patient suffering from a solid tumor, comprising administering an amount of a tissue transglutaminase sufficient to slow the growth of a solid tumor and inhibit angiogenesis in the vicinity of the tumor, wherein the administration comprises injecting into the tumor a dose of the tissue transglutaminase on five different days.

2. The method of claim 1 wherein the transglutaminase is human tissue transglutaminase.

3. The method of claim 1 wherein the tissue transglutaminase is obtained from mammalian tissue or cells.

4. The method of claim 1 wherein the tissue transglutaminase is a recombinant transglutaminase.

5. The method of claim 1, wherein the amount of tissue transglutaminase is sufficient to slow the growth of the solid tumor for at least 20 days from administration of a fifth dose.

6. The method of claim 1, wherein each dose of tissue transglutaminase is sufficient to produce a transglutaminase concentration of 50 µg/ml to 16 mg/ml at the site of the solid tumor.

* * * * *